(12) United States Patent
Jacobi et al.

(10) Patent No.: US 10,080,719 B2
(45) Date of Patent: *Sep. 25, 2018

(54) ALLERGEN DOSAGE FORM

(71) Applicant: ALK-Abello A/S, Horsholm (DK)

(72) Inventors: Henrik Hugo Jacobi, Vedbaek (DK); Annette Roemmelmayer Lundegaard, Soborg (DK); Christian Gauguin Houghton, Gentofte (DK); Stig Aasmul-Olsen, Skodsborg (DK); Lise Lund Maerkedahl, Fredensborg (DK); Jan Sondergaard Andersen, Hillerod (DK)

(73) Assignee: ALK-ABELLÓ A/S, Horshølm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/202,722

(22) Filed: Jul. 6, 2016

(65) Prior Publication Data

US 2016/0324767 A1 Nov. 10, 2016

Related U.S. Application Data

(60) Continuation of application No. 12/098,150, filed on Apr. 4, 2008, now Pat. No. 9,415,015, which is a division of application No. 10/723,308, filed on Nov. 26, 2003.

(60) Provisional application No. 60/429,086, filed on Nov. 26, 2002.

(30) Foreign Application Priority Data

Nov. 26, 2002 (DK) .................. 2002 01825
Feb. 24, 2003 (DK) .................. 2003 00279

(51) Int. Cl.
| | |
|---|---|
| A61K 9/00 | (2006.01) |
| A61K 39/36 | (2006.01) |
| A61K 9/20 | (2006.01) |
| A61K 39/35 | (2006.01) |
| A61K 45/06 | (2006.01) |
| A61J 1/03 | (2006.01) |
| A61K 9/19 | (2006.01) |
| A61K 9/70 | (2006.01) |
| A61K 39/39 | (2006.01) |
| B65D 75/32 | (2006.01) |
| G01N 33/15 | (2006.01) |
| G01N 33/94 | (2006.01) |
| A61K 39/00 | (2006.01) |

(52) U.S. Cl.
CPC .............. *A61K 9/006* (2013.01); *A61J 1/035* (2013.01); *A61K 9/0056* (2013.01); *A61K 9/19* (2013.01); *A61K 9/2018* (2013.01); *A61K 9/2063* (2013.01); *A61K 9/2095* (2013.01); *A61K 9/7007* (2013.01); *A61K 39/35* (2013.01); *A61K 39/36* (2013.01); *A61K 39/39* (2013.01); *A61K 45/06* (2013.01); *B65D 75/327* (2013.01); *G01N 33/15* (2013.01); *G01N 33/94* (2013.01); *A61K 2039/542* (2013.01); *A61K 2039/545* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 4,371,513 A | 2/1983 | Sanchez et al. |
| 4,371,516 A | 2/1983 | Gregory et al. |
| 5,244,663 A | 9/1993 | Bruttmann et al. |
| 5,343,672 A | 9/1994 | Kearney et al. |
| 5,729,958 A | 3/1998 | Kearney et al. |
| 5,762,961 A | 6/1998 | Roser et al. |
| 5,811,128 A | 9/1998 | Tice et al. |
| 6,471,992 B1 | 10/2002 | Yoo et al. |
| 6,919,086 B1 | 7/2005 | Kahlert et al. |
| 7,025,964 B1 | 4/2006 | Sone et al. |
| 8,012,505 B2 | 9/2011 | Houghton et al. |
| 8,329,196 B2 | 12/2012 | Jacobi et al. |
| 2002/0114833 A1 | 8/2002 | Abu-Izza et al. |
| 2002/0197321 A1 | 12/2002 | Seager |

FOREIGN PATENT DOCUMENTS

| | | |
|---|---|---|
| DE | 107 208 | 7/1974 |
| DE | 101 37 232 A1 | 2/2003 |
| EP | 0 271 079 A1 | 6/1988 |
| EP | 0 278 877 A1 | 8/1988 |
| EP | 0 346 622 A2 | 12/1989 |
| GB | 2378383 | 2/2003 |

(Continued)

OTHER PUBLICATIONS

Yasueda et al., Clinical and Experimental Allergy (1996), vol. 26, pp. 171-177.*

(Continued)

*Primary Examiner* — Hasan S Ahmed
*Assistant Examiner* — Frank Choi
(74) *Attorney, Agent, or Firm* — Womble Bond Dickinson (US) LLP

(57) ABSTRACT

The invention provides allergen containing pharmaceutical products and in particular fast-dispersing solid allergen dosage forms. In particular, fast-dispersing, non-compressed solid dosage forms suitable for oromucosal administration comprising a matrix and at least one allergen are provided. Suitable matrices are gelatine, starch and mannitol. Methods for the dosage forms are also provided.

23 Claims, No Drawings

(56) References Cited

FOREIGN PATENT DOCUMENTS

| | | |
|---|---|---|
| GB | 2 360 210 B1 | 12/2004 |
| JP | 0 537 070 A1 | 4/1993 |
| JP | 7-508019 | 9/1995 |
| JP | 09-176044 | 7/1997 |
| JP | 2002-511842 A | 4/2002 |
| JP | 2002-524469 | 8/2002 |
| WO | WO 91/09591 A1 | 7/1991 |
| WO | WO 93/19741 A1 | 10/1993 |
| WO | WO 93/23017 A1 | 11/1993 |
| WO | WO 97/39698 A1 | 10/1997 |
| WO | WO 98/20902 A1 | 5/1998 |
| WO | WO 98/43657 | 10/1998 |
| WO | WO 99/21579 A1 | 5/1999 |
| WO | WO 99/47680 A1 | 9/1999 |
| WO | WO 00/14114 A1 | 3/2000 |
| WO | WO 00/44351 | 8/2000 |
| WO | WO 00/51568 A1 | 9/2000 |
| WO | WO 00/51593 A2 | 9/2000 |
| WO | WO 00/61117 A1 | 10/2000 |
| WO | WO 0057856 | 10/2000 |
| WO | WO 200072003 | 11/2000 |
| WO | WO 01/39800 A2 | 6/2001 |
| WO | WO 01/51082 A1 | 7/2001 |
| WO | WO 01/56611 A1 | 8/2001 |
| WO | WO 02/13858 A1 | 2/2002 |
| WO | WO 02/40676 A2 | 5/2002 |
| WO | WO 03/096869 A2 | 11/2003 |

OTHER PUBLICATIONS

Abecassis, et al., "Fabrication du medicament homeopathique," pp. 77-79.
Allergy Principles and Practice, 1993, vol. 1, Fourth Edition, p. 520.
Beers, M., et al., "Hypersensitivity Disorders," Chapter 148, *The Merck Manual*, 1999, vol. 17, 1041-1067, Merck & Co.
Bernstein, et al., Twelve-year survey of fatal reactions to allergy injections and skin testing: 1990-2001, *J Allergy Clin Immunol*, (2004) vol. 113, pp. 1129-1136.
Bogner, R., et al., "Fast-dissolving tablets," *U.S. Pharmacist*, 2002.
Bousquet, T., et al., "WHO Position Paper. Allergen immunotherapy: therapeutic vaccines for allergic diseases," *Allergy*, 1998, vol. 53 (Suppl. 44), pp. 1-42.
Bousquet, et al, "Allergic Rhinitis and Its Impact on Asthma," *The Journal of Allergy and Clinical Immunology*, 2001, Suppl. to vol. 108(5), pp. S147-S344.
Bousquet, P., et al., "Sub-ingual Immunotherapy," World Allergy Organization Position Paper, *WAO Journal*, 2009, pp. 233-281.
Bufe, et al., Safety and efficacy in children of an Sa-standardized grass allergen tablet for sublingual immunotherapy, *J Allergy Clin Immunol*, 2009, vol. 123, pp. 167-173.
Chr. Hansen Group, Announcement of ALK-Abello's Pipeline, Announcement No. 14 of 27, 2001.
Chr. Hansen Group, Improving the Quality of Food and Health for People all Over the World, Annual Report, 2001, pp. 27-28.
Cleland et al., *Journal of Pharmaceutical Sciences*, 2001, vol. 90(3), pp. 310-321.
Committee for Proprietary Medicinal Products (CPMP), London, 1996, pp. 1-6.
Cox, et al., "Allergen immunotherapy: A practice parameter third update," *J Allergy Clin Immunol*, 2011, vol. 127, pp. ss1-s55.
Dahl, et al., "Specific immunotheraspy with SO standardized grass allergen tablets in asthmatics with rhinoconjunctivitis," *Allergy*, 2006, vol. 61, pp. 185-190.
Dahl, et al., "Efficacy and safety of subingual immunotherapy with grass allergen tablets for seasonal allergic rhinoconjunctivitis," *J Allergy Clin Immunol*, 2006, vol. 118, pp. 434-440.
Database WPI Section Ch, Week 197437 Derwent Publications Ltd. XP002257644, 1974, abstract.
Durham, S., et al., "Long-Term Clinical Efficacy of Grass-Pollen Immunotherapy," *The New England Journal of Medicine*, 1999, p. 468,474.
Durham, et al., "Sublingual immunotherapy with once-daily grass-allergen tablets: a randomised controlled trial in seasonal allergic rhinoconjunctivitis," *J Allergy Clin Immunol*, 2006, vol. 20(117), pp. 802-809.
Durham, et al, "Long-term clinical effect in grass pollen-induced rhinoconjunctivitis after treatment with SOI-standardized grass allergy immunotherapy tablet," *J. Allergy Clin Immunol.*, 2010, vol. 125, pp. 131-138.
Durham, et al., "SQ-standardized sublingual grass immunotherapy: Confirmation of disease modification 2 years after 3 years of treatment in a randomized trial," *J Allergy Clin Immunol*, 2012, vol. 129, pp. 717-725.
Elisa Competition Assay, "Quantitative determination of relative potency of allergenic extracts," 1993, pp. 15-25.
Emminger, et al., Progressive effect of grass tablet immunotherapy during long-term treatment in patients with rhinoconjunctivitis, *Allergy*, 2007, vol. 62 (Suppl. 83) abstract 663, p. 240.
European Pharmacopoeia, third edition, 1996, p. 66.
European Pharmacopoeia, third edition, Monograph 1063, "Allergen Products," 1977, pp. 356-358.
European Pharmacopoeia, third edition, 1997, Pharmaceutical Technical Procedures, pp. 134-135.
The European Agency for the Evaluation of Medicinal Products, Human Medicines Evaluation Unit, Committee for Proprietary Medicinal Products (CPMP), London, 1996, pp. 1-6.
Frew, "Sublingual immunotherapy," *J Allergy Clin Immunol*, 2001, vol. 107, pp. 441-444.
Fu, et al., "Orally fast disintegrating tablets: developments, technologies, taste-masking and clinical studies," *Critical Reviews in Therapeutic Drug Carrier Systems*, 2004, vol. 21, pp. 433-475.
Kearney, P., "The Zydis Oral Fast-Dissolving Dosage Form," Chapter 13, *Drugs and the Pharmaceutical Sciences*, 2003, vol. 126, Modified-Release Drug Delivery Technology, J.J. Rathbone et al. (eds), Marcel Dekker, Inc., New York, NY.
Lima, et al, "Grass pollen sublingual immunotherapy for seasonal rhinoconjunctivitis: a randomized controlled trial," *Clin Exp Allergy*, 2002, vol. 32(4), abstract.
Gina (Global Initiative for Asthma, "Global Strategy for Asthma Management and Prevention," updated 2003, 180 pages.
Guerra, L., et al., "Randomized open comparison of the safety of SLIT in a no updosing and traditional updosing schedule in patient with Parietaria allergy," *Allergoimmunopathol*, 2006, vol. 34, pp. 821-823.
Haugaard, L., et al., "A controlled dose-response study of immunotherapy with standardized, partially purified extract of house dust mite: Clinical efficacy and side effects," *J Allergy Clin Immunol*, 1993, vol. 91(3), pp. 7090-722.
Hill, et al, "The ACVD task force on canine atopic dermatitis (IV): Environmental allergens," *Vetrinary Immunology and Immunopathology* 2001, vol. 81, pp. 169-186.
Hordijk, et al, Allergol. Immunopathol. (Madr) (1998),vol. 26, No. 5, pp. 234-240 [retrieved on Dec. 1, 2008].
ICH Harmonised Tropartite Guideline, "Stability Testing of New Drug Substances and Products Q1A(R2)," International Conference on Harmonisation of Technical Requirements for Registration of Pharmaceuticals for Human Use, 1993, pp. 1-5.
Ipsen, H., et al., "Allergenic Extracts," *Basic Science, Part I*, Chapter 20,pp. 540-547.
Kapp, et al., "Sublingual grass tablet immunotherapy shows a progressive immunological effect," *Allergy*, 2007, vol. 62 (Suppl. 83) abstract 658, p. 238.
Lafarma Product Insert and Translation, 2000, 8 pages
Larsen, et al., "Manufacturing and standardizing Allergen Extracts in Europe," Chapter 23 in *Allergens and Allergen Immunotherapy*, 3rd Edition, Revised and Expanded, Richard F. Lockey, Samuel C. Bukantz and Jean Bousquet (eds.), Marcel Dekker, Inc., New York, 2004, pp. 433-456.
Leung, et al., "Disease modification of allergic rhinoconjunctivitis by using sublingual grass immunotherapy," *J Allergy Clin Immunol*, 2012, vol. 129, p. 653.
Lombardi, et al., "Administration regimens for sublingual immunotherapy to pollen allergens: What do we know?," *Allergy*, 2009, vol. 64, pp. 849-854.

(56) References Cited

OTHER PUBLICATIONS

Lowenstein, H., "Physico-Chemical and Immunochemical Methods for the Control of Potency and Quality of Allergenic Extracts," *Regulatory Control and Standardization of Allergenic Extracts*, First International Paul-Ehrlich-Seminar, 1979, pp. 122-132.

Moreno-Ancillo, et al., Efficacy and quality of life with once-daily sublingual immunotherapy with grasses plus olive pollen extract without updosing, *J Investig Allergol Clin Immunol*, 2007, vol. 17, pp. 399-405.

Nelson, H., et al., "A double-blind, placebo-controlled evaluation of sublingual immunotherapy with standardized cat extract," *J Allergy Clin Immunol*, 1993, vol. 92(2), pp. 229-236.

Oppenheimer, J., et al., "Safety and efficacy of oral immunotherapy with standardized cat extract," *J Allergy Clin Immunol*, 1994, vol. 93(1, part 1), pp. 61-67.

Parakh, S., et al., "A Review of Mouth Dissolving Tablet Technologies," *Pharmaceutical Technology*, 2003, pp. 92-100.

Pradalier, A., et al., "Sublingual-swallow Immunotherapy (SLIT) with a Standardized Five-grass Pollen Extract (drops and Sublingual Tablets) versus Placebo in Seasonal Rhinitis," *Allergy*, 1999, vol. 54, pp. 819-828.

Rak, et al., Grass tablet immunotherapy consistently relieves seasonal eye and nasal symptoms (including blocked nose) in consecutive seasons, *Allergy*, 2007, vol. 62(Suppl. 83) abstract 656, p. 237.

Ramirez, J., et al., "Group 5 determination in Pooideae grass pollen extracts by monoclonal antibody-based ELISA Correlation with biologic activity," *Allergy*, 1997, vol. 52, pp. 802-813.

Reid, et al., Survey of fatalities from skin testing and immunotherapy, *J Allergy Clin Immunol*, 1993, vol. 92, pp. 6-15.

*Remington's Pharmaceutical Sciences* ($17^{th}$ Ed. 1985), pp. 1478-1480, 1482-1484.

*Remington's Pharmaceutical Sciences* ($17^{th}$ Ed. 1985), pp. 1777, 1787-1789.

Rodriquez, et al., Once daily sublingual immunotherapy without upsdosing—a new treatment schedule, *Int Arch Allerg Immunol*, 2006, vol. 140, pp. 321-326.

Seager, H., "Drug-delivery Products and the Zydis Fast-dissolving Dosage Form," *J. Pharm. Pharmacol.*, 1988, vol. 50, pp. 375-382.

STN online, file DISSABS, Acc. No. 93:47693 (Cho et al., Dissertation Abstracts International (1993), vol. 54, No. 4B, p. 1940).

USP NF, Tablet Friability, The Official Compendia of Standards, 2003, Section 1216, p. 2439.

Veb Sachsisches Serum, "Buccal medicament dosage forms—dissolving in the saliva and resorbed in the mouth," No. Abstract, DD-107208, XP-002257644.

Wahn, et al., "Efficacy and safety of 5 grass pollen sublingualimmunotherapy in pediatric allergic rhinoconjunctivitis," *J Allergy Clin Immunol*, 2009, vol. 123, pp. 160-166.

* cited by examiner

ALLERGEN DOSAGE FORM

This application is a continuation of U.S. patent application Ser. No. 12/098,150, which is a divisional of U.S. patent application Ser. No. 10/723,308, filed Nov. 26, 2003, which claims the benefit of U.S. Provisional Application Ser. No. 60/429,086, filed Nov. 26, 2002, Danish Patent Application PA 200201825, filed Nov. 26, 2002, and Danish Patent Application PA 200300279, filed Feb. 24, 2003. Each of these priority applications is incorporated herein by reference in their entirety.

FIELD OF THE INVENTION

This invention relates to an allergen containing pharmaceutical product and in particular to fast-dispersing solid allergen dosage forms and a method for preparing such dosage forms.

BACKGROUND OF THE INVENTION

Allergy is a major health problem in countries where Western lifestyle is adapted. Furthermore, the prevalence of allergic disease is increasing in these countries. Although allergy in general may not be considered a life-threatening disease, asthma annually causes a significant number of deaths. An exceptional prevalence in about 30% of teenagers conveys a substantial loss in quality of life, working days and money, and warrants a classification among major health problems in the Western world.

Allergy is a complex disease. Many factors contribute to the sensitisation event. Among these is the susceptibility of the individual defined by an as yet insufficiently understood interplay between several genes. Another important factor is allergen exposure above certain thresholds. Several environmental factors may be important in the sensitisation process including pollution, childhood infections, parasite infections, intestinal microorganisms, etc. Once an individual is sensitised and the allergic immune response established, the presence of only minute amounts of allergen is efficiently translated into symptoms.

The natural course of allergic disease is usually accompanied by aggravation at two levels. First, there is a progression of symptoms and disease severity. For example, there is a progression from hay fever to asthma. Secondly, dissemination in offending allergens most often occurs resulting in allergic multi-reactivity. Chronic inflammation leads to a general weakening of the mucosal defense mechanisms resulting in unspecific irritation and eventually destruction of the mucosal tissue. Infants may become sensitised primarily to foods, i.e. milk, resulting in eczema or gastrointestinal disorders; however, most often they outgrow these symptoms spontaneously. These infants are at risk of developing inhalation allergy later in their lives.

The most important allergen sources are found among the most prevalent particles of a certain size in the air we breathe. These sources are remarkably universal and include grass pollens and house dust mite faecal particles, which together are responsible for approximately 50% of all allergies. Of global importance are also animal dander, i.e. cat and dog dander, other pollens, such as mugwort pollens, and micro-fungi, such as *Alternaria*. On a regional basis other pollens may dominate, such as birch pollen in Northern and Central Europe, ragweed in the Eastern and Central United States, and Japanese cedar pollen in Japan. Insects, i.e. bee and wasp venoms, and foods each account for approximately 2% of all allergies.

Allergy, i.e. type I hyper-sensitivity, is caused by an inappropriate immunological reaction to foreign non-pathogenic substances. Important clinical manifestations of allergy include asthma, hay fever, eczema, and gastro intestinal disorders. The allergic reaction is prompt and peaks within 20 minutes upon contact with the offending allergen. Furthermore, the allergic reaction is specific in the sense that a particular individual is sensitised to particular allergen(s), whereas the individual does not necessarily show an allergic reaction to other substances known to cause allergic disease. The allergic phenotype is characterized by a pronounced inflammation of the mucosa of the target organ and by the presence of allergen specific antibody of the IgE class in the circulation and on the surfaced of mast-cells and basophils.

An allergic attack is initiated by the reaction of the foreign allergen with allergen specific IgE antibodies, when the antibodies are bound to high affinity IgE specific receptors on the surface of mast-cells and basophils. The mast-cells and basophils contain preformed mediators, i.e. histamine, tryptase, and other substances, which are released upon cross-linking of two or more receptor-bound IgE antibodies. IgE antibodies are cross-linked by the simultaneous binding of one allergen molecule. The cross-linking of receptor bound IgE on the surface of mast-cells also leads to release of signalling molecules responsible for the attraction of eosinophils, allergen specific T-cells, and other types of cells to the site of the allergic response. These cells in interplay with allergen, IgE and effector cells, lead to a renewed flash of symptoms occurring 12-24 hours after allergen encounter (late phase reaction).

Allergy disease management comprises diagnosis and treatment including prophylactic treatments. Diagnosis of allergy is concerned with the demonstration of allergen specific IgE and identification of the allergen source. In many cases a careful anamnesis may be sufficient for the diagnosis of allergy and for the identification of the offending allergen source material. Most often, however, the diagnosis is supported by objective measures, such as skin prick test, blood test, or provocation test.

The therapeutic options fall in three major categories. The first opportunity is allergen avoidance or reduction of the exposure. Whereas allergen avoidance is obvious e.g. in the case of food allergens, it may be difficult or expensive, as for house dust mite allergens, or it may be impossible, as for pollen allergens. The second and most widely used therapeutic option is the prescription of classical symptomatic drugs like anti-histamines and steroids. Symptomatic drugs are safe and efficient; however, they do not alter the natural cause of the disease, and they do not control the disease dissemination. The third therapeutic alternative is specific allergy vaccination that in most cases reduces or alleviates the allergic symptoms caused by the allergen in question.

Conventional specific allergy vaccination is a causal treatment for allergic disease. It interferes with basic immunological mechanisms resulting in persistent improvement of the patients' immune status. Thus, the protective effect of specific allergy vaccination extends beyond the treatment period in contrast to symptomatic drug treatment. Some patients receiving the treatment are cured, and in addition, most patients experience a relief in disease severity and symptoms experienced, or at least an arrest in disease aggravation. Thus, specific allergy vaccination has preventive effects reducing the risk of hay fever developing into asthma, and reducing the risk of developing new sensitivities.

The immunological mechanism underlying successful allergy vaccination is not known in detail. A specific immune response, such as the production of antibodies against a particular pathogen, is known as an adaptive immune response. This response can be distinguished from the innate immune response, which is an unspecific reaction towards pathogens. An allergy vaccine is bound to address the adaptive immune response, which includes cells and molecules with antigen specificity, such as T-cells and the antibody producing B-cells. B-cells cannot mature into antibody producing cells without help from T-cells of the corresponding specificity. T-cells that participate in the stimulation of allergic immune responses are primarily of the Th2 type. Establishment of a new balance between Th1 and Th2 cells has been proposed to be beneficial and central to the immunological mechanism of specific allergy vaccination. Whether this is brought about by a reduction in Th2 cells, a shift from Th2 to Th1 cells, or an up-regulation of Th1 cells is controversial. Recently, regulatory T-cells have been proposed to be important for the mechanism of allergy vaccination. According to this model regulatory T-cells, i.e. Th3 or Tr1 cells, down-regulate both Th1 and Th2 cells of the corresponding antigen specificity. In spite of these ambiguities it is generally believed that an active vaccine must have the capacity to stimulate allergen specific T-cells, preferably TH1 cells.

Primarily for two reasons specific allergy vaccination in spite of its virtues, is not in widespread use. One reason is the inconveniences associated with the traditional vaccination programme that comprises repeated vaccinations, such as injections over several months. The other reason is, more importantly, the risk of allergic side reactions. Ordinary vaccinations against infectious agents are efficiently performed using a single or a few high dose immunizations. This strategy, however, cannot be used for allergy vaccination since a pathological immune response is already ongoing.

Conventional specific allergy vaccination is therefore carried out using multiple subcutaneous immunizations applied over an extended time period. The course is divided in two phases, the up dosing and the maintenance phase. In the up dosing phase increasing doses are applied, typically over a 16-week period, starting with minute doses. When the recommended maintenance dose is reached, this dose is applied for the maintenance phase, typically with injections every six weeks. Following each injection the patient must remain under medical attendance for 30 minutes due to the risk of anaphylactic side reactions, which in principle although extremely rare could be life-threatening. In addition, the clinic should be equipped to support emergency treatment. There is no doubt that a vaccine based on a different route of administration would eliminate or reduce the risk for allergic side reactions inherent in the current subcutaneous based vaccine as well as would facilitate a more widespread use, possibly even enabling self vaccination at home.

Attempts to improve vaccines for specific allergy vaccination have been performed for over 30 years and include multifarious approaches. Several approaches have addressed the allergen itself through modification of the IgE reactivity. Others have addressed this route of administration.

The immune system is accessible through the oral cavity and oromucosal, e.g. sublingual administration, of allergens is a known route of administration.

Conventionally, allergy vaccine using the oromucosal route consists of the periodic dosing of a solution of the allergen at intervals spaced apart by at least one day. In comparison, the therapeutic (accumulated) maintenance doses given exceeded the maintenance of the comparable subcutaneous dose by a factor of 5-500. Obvious drawbacks of this dosage form and route of administration are the problems associated with accurate and uniform self administration of the correct dose by the patient (several drops may have to be given, uniformity of the individual drops, application site accuracy, etc.). Additionally, there is a need to refrigerate the drug and include preservatives in the formulation.

Netien et al. ("Galenica 16—Médicaments homéopathiques" ed. 2, 1986, pages 77-99) discloses a liquid solution impregnated onto a solid particulate (granules) or conventional compressed tablets of lactose, saccharose or a mixtures of these for sublingual administration of medicaments such as allergens.

DD-A.0 107 208 discloses a process for preparing a conventional compressed tablet containing an allergen. Upon administration the tablet is dissolved by the saliva and the allergen is then absorbed through the mucosa of the oral cavity. The formulation contains a water insoluble excipient, namely talcum as well as paraffin and fatty acids which is not desirable because it will leave an unpleasant remnant in the mouth of the patient. Moreover, the friction produced during the tabletting process may be detrimental to the physical stability of the allergens EP 278 877 discloses a pharmaceutical composition for sublingual use, where a solid support is coated with a solution of an allergen when spraying the solution onto solid support globules. The resulting formulation is alleged to disintegrate rapidly, but not instantaneously. However, there is no disclosure of how to achieve the objective. Moreover, the formulation contains reducing sugars in the form of lactose, which are prone to react with allergens.

In order to ensure that as much as possible of an administered dose of a certain allergen is presented to the mucosa of the oral cavity and additionally that the contact time of the disintegrated product with the mucosa is maximised, it is very important that the dosage form disintegrates instantaneously upon contact with the saliva of the oral cavity. Fast dispersing solid dosage forms, which readily release the active ingredient in the oral cavity are known in the art.

U.S. Pat. No. 4,371,516 discloses pharmaceutical dosage forms containing active ingredients, which disintegrate rapidly in water. The pharmaceutical dosage forms comprise an open matrix network of carrier material, which disintegrate within 10 seconds.

A freeze-dried fish gelatine based carrier as disclosed in WO 00/61117 is designed to release the active ingredient instantaneously upon contact with saliva when administered in the oral cavity.

A freeze-dried modified starch carrier as disclosed in WO 00/44351 is designed to release the active ingredient instantaneously upon contact with saliva when administered in the oral cavity.

WO 99/21579 discloses a fast-dispersing dosage form comprising a vaccine and an adjuvant for oral use.

WO 02/13858 discloses fast dissolving pharmaceutical composition containing vaccines in the form of a fast dissolving "cake" for oral use. The object of WO 02/13858 appears to be to provide viral or bacterial vaccines that will stay intact in the gastrointestinal tract. This is achieved by protecting the antigen against the acidic content of the stomach by incorporating antacids such as calcium carbonate into the cake.

WO 00/51568 discloses a fast-disintegrating compressed low friability tablet that is designed to dissolve in the mouth in contact with saliva in less than 30 seconds forming an easy-to-swallow suspension.

It is alleged in U.S. Pat. No. 4,371,516 that the formulation is useful for oral vaccines. In the case of WO 00/61117, WO 00/44351, WO 99/21579 and WO 02/13858, it is also alleged that the inventions are directed to non-infections immuno-modulated conditions such as systemic allergic conditions e.g. hayfever. However, there is no disclosure in any of these applications of technical information or examples of how a fast-dispersing allergen vaccine solid dosage form can be manufactured. For example, there are no indications of an appropriate dosage of a certain allergen in any of the disclosed formulation. It is very important to administer a correct dosage of an allergen to a patient, because an excess dose may induce anaphylactic shock in the patient. Furthermore, no recognition of or indications of appropriate measures in relation to stability or friability of such formulations are given.

SUMMARY OF THE INVENTION

The present invention concerns a pharmaceutical product suitable for oromucosal administration of an allergen comprising at least one allergen and a matrix in form of a fast-dispersing non-compressed solid dosage form characterized in that the allergen containing dosage form is stable, sufficiently robust and does not release hazardous amounts of allergen residues upon handling by the patient.

Further, a fast-dispersing non-compressed solid dosage form suitable for oromucosal administration comprising a matrix forming agent and an allergen wherein the allergen is stable and the dosage form has a low friability with respect to allergen release, the dosage form dissolves quickly and does not require an adjuvant.

In particular the invention concerns a pharmaceutical product suitable for administration of allergen comprising
 a fast-dispersing, non-compressed solid dosage form suitable for oromucosal administration including:
  a) a matrix formed from at least one matrix-forming agent, and
  b) an effective dose of an allergen for desensitizing an individual to said allergen,
 wherein
  (c) the loss of the allergen content in said dosage form is less than 50% of the initial allergen content after being held for 3 months at 25° C. and 60% relative humidity, and
  (d) the loss of allergen from said solid dosage form is less than about 0.5 µg allergen extract or less than about 0.05 µg major allergen when subjected to a friability test.

In one preferred embodiment of the invention, the solid dosage form comprises fish gelatine and mannitol as matrix-forming agents.

In another preferred embodiment of the invention, the solid dosage form comprises starch and mannitol as matrix forming agents.

The present invention also provides methods of producing these solid dosage forms and methods of treating allergy by administration of these solid dosage forms.

DETAILED DESCRIPTION OF THE INVENTION

The present invention is based on a number of surprising findings, none of which could with a reasonable expectation of success be predicted a priori. First, it is based on the finding that it is possible to use a fast-dispersing, non-compressed dosage form for administration of an allergen, and that it is possible to obtain an effective allergy treatment by the use of such a formulation. In particular, it has been shown that it is indeed possible to obtain delivery of a sufficient amount of allergen to the immune system of the patient via the oromucosal route using a fast-dispersing non-compressed solid dosage form without eliciting an undesirable level of side effects. Moreover, the present invention has provided the relevant dose levels for obtaining a therapeutic effect without unacceptable side effects.

Secondly, the invention is based on the finding that an effective treatment can be obtained by the use of a fast-dispersing, non-compressed dosage form without the use of an adjuvant.

Thirdly, the invention is based on the finding that it is possible to formulate an allergen as a fast-dispersing, non-compressed dosage form while meeting the special demands required by an allergen with respect to stability and low friability. In particular, it has been shown that it is possible to balance the oppositely directed requirements that the dosage form should be fast-dispersing on the one side and both stable and have low-friability on the other side so as to obtain a dosage form, which to a sufficient extent is fast-dispersing, stable and has low friablility.

Allergen proteins are susceptible to degradation that is influenced by a number of factors of the environments they are contained in. It is sought that it is pertinent for allergy treatment and in particular to allergy vaccination that the allergen is delivered intact to the immune system in therapeutically relevant doses. Thus, the allergen must remain stable during production, storage and use. The present work has shown that it is in fact possible to formulate allergen proteins in a fast-dispersing, non-compressed dosage form which is stable in respect to allergen doses and allergen activity. Moreover, it has surprisingly been found that these formulations are indeed stable at room temperature. This finding has significant importance for the handling procedures of the final product. Cold storage at the manufacturing plant, during transport or during storage at the pharmacy is often associated with high cost, because the cooling facilities have to be closely monitored and it is very expensive to invest in reliable cooling facilities. Moreover, with respect to compliance of the patient, it is also preferable that the dosage form can be stored at room temperature.

Thus, present work has shown that it is in fact possible to formulate allergen proteins in a fast-dispersing, non-compressed dosage form being therapeutically effective without the need for an adjuvant. Further such allergen containing solid dosage forms are furthermore stable at advantageous conditions.

When allergen proteins are formulated in a fast-dispersing, non-compressed dosage form, it is further advantageous that the resulting dosage form does not substantially release the allergens to the surrounding environment or to a person handling the dosage form upon direct contact. A priori non-compressed fast-dispersing solid dosage forms are characterized by a low mechanical strength compared to compressed tablets due to the inherent nature of the non-compressed matrix, which is fragile and brittle, almost wafer-like. During e.g. packing, storage, transport and handling of the dosage form by the patient, residual particles containing the allergen may be released to the environment and patient. This is especially detrimental when the active ingredient is an allergen, because the allergen can elicit an allergic reaction in a disposed person or induce an allergic reaction, such sensitisation or allergic response being dose dependent. Maximum allowable levels for environmental contamination in the form of e.g. allergen in dust have been proposed, depending on the allergen in question, to be as low as 2 micrograms major allergen per gram house dust. (Allergy. Principles and practice (1993, 4. ed.), Mosby-Year book, Vol. I page 520).

Non-compressed fast-dispersing solid dosage forms, which are manufactured by removal of a liquid from a solidified system comprising matrix forming agents, active ingredient and other optional agents, preferably are manufactured in situ. The in situ manufacturing process generally involves removal of solvent from a solidified system of the active ingredient and the matrix forming excipients within the final container such as a blister pack. The in situ technique used commercially does not allow for conventional coating of the dosage form. Application of a coating of the dosage form would in most cases affect dispersing of the solid dosage form, thus jeopardizing the instantaneous release properties of the dosage form.

Therefore, despite the opposite nature of these requirements, the present work has shown that it is in fact possible to formulate effective dosages of allergen proteins in a fast-dispersing, non-compressed dosage form, while at the same time obtaining low-friability and maintaining the fast-dispersing property.

All of the above findings are supported by experimental laboratory work or pre-clinical experiments using test animals, where applicable, or clinical trials, where applicable.

The term "fast-dispersing dosage form" refers to dosage forms which disintegrate in less than about 90 seconds, preferably in less than about 60 seconds, preferably in less than about 30 seconds, more preferably in less than about 20, even more preferably in less than about 10 seconds in the oral cavity, even more preferred in less than about 5 seconds, and most preferably in less than about 2 seconds after being received in the oral cavity. The solid dosage form of the invention may be in the form of tablets, capsules, lozenges or caplets.

The term "non-compressed" refers to a solid dosage form, which is manufactured by removal of a liquid from a solidified system comprising matrix forming agents, active ingredient and other suitable ingredients resulting in an allergen comprised solid matrix.

The term "solid dosage form" refers to a unit dosage form that is not a liquid, or a powder when it is administered in the oral cavity, thus "solid dosage forms" refers to e.g. tablets containing a unit dose of the active ingredient.

The term tablets, solid dosage and vaccine form are used interchangeably herein.

The term "matrix forming agent" refers to any pharmaceutically acceptable water-soluble or water-dispersible excipient that will serve as a carrier for the active ingredient in the solid dosage form.

The term "excipient" refers to any ingredient that may be added to the formulation besides the active ingredient.

The term "loss of the allergen content in said dosage form" refers to for example degradation or inactivation of the allergen in the dosage form during for example storage, transportation and use. The loss may be determined as either the loss in biological activity/potency or as the loss in the actual content of the allergen. Preferably, the loss of the allergen content is measured as the loss of at least one major allergen. The loss may for example be measured in an ELISA method as described in Obispo et al. (Allergy, 1997, 52, pg. 806-813 using allergen specific reagents).

The term "loss of the allergen content from said dosage form" refers to for example release of the allergen in the dosage form during, for example storage, transportation and use. The loss may be determined as either the loss in biological acticivity/potency or as the loss in the actual content of the allergen. Preferably, the loss of the allergen content is measured as the loss of at least one major allergen. The loss may for example be measured in an ELISA method as described in Obispo et al. (Allergy, 1997, 52, pg. 806-813 using allergen specific reagents).

The term "stable" refers to dosage forms where the loss in allergen content is less than 50% of the initial content after being stored for 3 months at 25° C. and 60% relative humidity in the final container either measured as the loss in biological acticivity/potency or as the loss in content of at least one major allergen. The loss may for example be measured in an ELISA method as described above.

The term "low friability" refers to the amount of allergen containing material that is lost from the dosage form when it is subjected to an external force. The solid dosage form has a sufficient friability and robustness to be transported, stored and handled if the allergen containing material lost contains less than 0.5 µg allergen extract or 0.05 µg major allergen per solid dosage form. For the purpose of the present invention, the friability may be measured by a method according to the present invention.

"Tensile strength $\sigma$" is calculated according to the following equation:

$$\sigma = 3 Wa \times 9.8 \text{ Nmm}^{-2}/2d^2 b$$

where w=Peak load to fracture (kgF)
a=distance between supports
d=thickness of the fast-dispersing solid dosage form (mm)
b=diameter of the fast-dispersing solid dosage form (mm)

"Peak load to fracture" means the peak force required to fracture a unit in a three point bend test using an appropriate instrument (e.g. CT5, Engineering Systems, 1 Loach Court, Radford Bridge Road, Nottingham NG8 1NA, UK).

The term "oromucosal administration" refers to a route of administration where the dosage form is placed under the tongue or anywhere else in the oral cavity to allow the active ingredient to come in contact with the mucosa of the oral cavity or the pharynx of the patient in order to obtain a local or systemic effect of the active ingredient. An example of an oromucosal administration route is sublingual administration.

The term "sublingual administration" refers to a route of administration, where a dosage form is placed underneath the tongue in order to obtain a local or systemic effect of the active ingredient.

The term "allergen" refers to any naturally occurring protein or mixtures of proteins that have been reported to induce allergic, i.e. IgE mediated reactions upon their repeated exposure to an individual. Examples of naturally occurring allergens include pollen allergens (tree, weed, herb and grass pollen allergens), mite allergens (from e.g. house dust mites and storage mites), insect allergens (inhalant, saliva- and venom origin allergens), animal allergens from e.g. saliva, hair and dander from e.g. dog, cat, horse, rat, mouse, etc., fungi allergens and food allergens. The allergen may be used in the form of an allergen extract, a purified allergen, a modified allergen or a recombinant allergen or a recombinant mutant allergen, any allergen fragment above 30 amino acids or any combination thereof.

The expression "allergen extract" as used therein refers to an extract obtained by extraction of a biological allergen source material as generally described in "Allergenic extracts", H. Ipsen et al, chapter 20 in Allergy, principle and practise (Ed. S. Manning) 1993, Mosby-Year Book, St. Louis. Such extract may be obtained by aqueous extraction of water soluble material followed by purification steps like filtration to obtain the solution i.e. the extract. The extract may then be subjected to further purification and/or processing like freeze-drying removing substantially all the water. Generally, an allergen extract comprises a mixture of proteins and other molecules. Allergen proteins are often classified as a major allergen, an intermediate allergen, a minor allergen or no classification. An allergen extract generally comprises both major and minor allergens. Major allergens will generally constitute approximately 5-15% of an average allergen extract, more often about 10%. Classification of an allergen is based on an assessment of the clinical importance of the particular allergen and is given below. Examples of important major allergen found in an extract include grass group 1 and 5 and 6 allergens (e.g. Phl p 1, 5, and 6), dust mite group 1 and 2 allergens (e.g. Der p 1, Der p 2), tree pollen allergen 1 (Bet v 1), cedar pollen allergen 1 and 2 (e.g. Cry j 1, Cry j 2), ragweed pollen 1 and 2 (Amb a 1, Amb a 2), cat allergen 1 (i.e. Fel d1). The average allergic person will be sensitised to and react to one or more major allergens and further may also be sensitised and react to minor allergens.

Amounts of allergen extract referred to herein refers to the dry matter content of such allergen extracts.

Preferably the water content of the dry matter does not exceed 10%, more preferably 5% by weight.

The expression "biological allergen source material" as used therein refers to any biological material comprising one or more allergens. Examples of such materials are acarids PMB (Pure Mite Body) or WMC (Whole Mite Culture), defatted or non-defatted pollens from e.g. grasses, herbs, weeds and trees, animal hair and dander, pelt, fungi mycelia and spores, insect bodies, venom or saliva and foods.

Biological allergen source materials may comprise contaminating materials, such as foreign pollen and plant and flower debris for an allergen pollen source material.

The degree of contamination should be minimised. Preferably, the content of contaminants should not exceed 10% (W/W) of the biological source material.

Normally an allergen extract contains at least 10% protein of the dry matter content of the allergen extract as determined in a standard protein assay such as BCA or Lowry and the remainder consists of other "non-protein material," which may be components such as lipids, carbohydrates, or bound water which originate from the biological allergen source.

An allergen extract may be formulated and stored in form of a freeze-dried material obtainable by freeze-drying a liquid allergen extract at a pressure of below 800 micro bar and for a period of up till 100 hours removing the water.

In the field of allergy extracts, there is no international accepted standardisation method. A number of different units of extract strength i.e. bio-potency exist. The methods employed and the units used normally measure the allergen content and biological activity. Examples hereof are SQ-Units (Standardised Quality units), BAU (Biological Allergen Units), BU (biological units), UM (Units of Mass), IU (International Units) and IR (Index of Reactivity). Hence, if extracts of origins other than those disclosed herein are used, they need to be standardised against extract disclosed herein in order to determine their potency in SQ units or any of the above mentioned units. The subject matter is dealt with in "Allergenic extracts", H. Ipsen et al, chapter 20 in Allergy, principle and practise (Ed. S. Manning) 1993, Mosby-Year Book, St. Louis and Lowenstein H. (1980) Arb Paul Ehrlich Inst 75:122.

The bio-potency, i.e. the in vivo allergenic activity, of a given extract depends on a number of factors, the most important being the content of major allergens in the extract, which varies with the composition of the biological source material.

The amount of allergen extract in grams to be used for obtaining a desired bio-potency varies with the type of extract in question, and for a given type of extract the amount of allergen extract varies from one batch to another with the actual bio-potency of the extract.

For a given batch of extract, the amount of allergen extract in grams to be used for obtaining a desired bio-potency may be determined using the following procedure:

(a) The bio-potency of various amounts of a reference extract is determined using one or more immunological in vivo tests to establish a relationship between bio-potency and amount of reference extract. Examples of the said immunological in vivo tests are Skin Prick Test (SPT), Conjunctival Provocation Test (CPT), Bronchial Challenge with Allergen (BCA) and various clinical trials in which one or more allergy symptoms is monitored, see for example e.g. Haugaard et al., J Allergy Clin Immunol, Vol. 91, No. 3, pp 709-722, March 1993.

(b) On the basis of the established relationship between bio-potency and reference extract, the bio-potency of one or more relevant doses for use in the dosage forms of the invention is selected with due consideration to a balance of the factors of i) the effect of treating or alleviating symptoms of allergy, ii) side effects recorded in the immunological in vivo tests, and iii) the variability of i) and ii) from one individual to another. The balancing is done to obtain a maximal adequate therapeutic effect without experiencing an unacceptable level of side effect. The way of balancing the factors are well known to those skilled in the art The bio-potency of the one or more relevant doses found may be expressed in any biopotency unit available, such as SQ units, BAU, IR units, IU, cf. above.

(c) From the reference extract one or more bio-potency reference standard extracts is prepared and, if used, the bio-potency unit values of the reference standard extracts are calculated on the basis of the bio-potency unit value allocated to the one or more relevant doses, e.g. such a standard for BAU can be obtained from FDA as illustrated below.

(d) For the reference standard extracts of each extract type, a number of parameters for evaluating the bio-potency of extracts are selected. Examples of such evaluation parameters are total allergenic activity, the amount of defined major allergens and overall molecular composition of the extract. The total allergenic activity may be measured using an in vitro competitive immunoassay, such as ELISA and MagicLite® luminescence immunoassay (LIA), using a standardised antibody mixture raised against the extract obtained using standard methods, e.g. antibodies raised in mouse or rabbit, or a pool of allergic patients sera. The content of major allergens may e.g. be quantified by rocket immuno-electrophoresis (RIE) and compared to the reference standards. The overall molecular composition may be examined using e.g. crossed immunoelectrophoresis (CIE) and sodium dodecyl sulphate polyacrylamide gel electrophoresis (SDS-PAGE).

(e) For a given batch of extract of unknown bio-potency (test extract), the amount of extract to be used for obtaining a desired bio-potency level (effective dose for use in the solid dosage form according to the present invention) may be determined as follows: For each evaluation parameter selected, the test extract is compared with the reference standard extracts using the relevant measurement methods as described above, and on the basis of the measurement results the amount of extract having the desired bio-potency is calculated.

SQ-Unit: The SQ-Unit is determined in accordance with ALK-Abelló A/S's "SQ biopotency"-standardisation method, where 100,000 SQ units equal the standard subcutaneous maintenance dose. Normally 1 mg of extract contains between 100,000 and 1,000,000 SQ-Units, depending on the allergen source from which they originate and the manufacturing process used. The precise allergen amount can be determined by means of immunoassay i.e. total major allergen content and total allergen activity.

BAU (Biological Allergen Units) is biological potency units as determined according to the requirements of the FDA for allergen product described in "Quantitative determination of relative potency of allergenic extracts" ("Methods of the allergen products testing Laboratory" "ELISA competition assay". Page 15, #49N-0012, FDA, October 1993). A dose of 100,000 SQ-Units containing grass extract equals a content of 2600-4700 BAU according to the method above. Likewise, other extracts can be assessed according to the method above.

The term "effective dose of an allergen for desensitization" shall mean a dose which when taken once or repeatedly in a monodose or in incremental doses results in, for example, an adaptive immune response and thus serves as means to desensitise allergic patients. Preferably, the term shall mean the amount of allergen in each dosage form necessary to induce an adaptive immune response after repeated administration of said solid dosage forms in accordance with a treatment regimen (over a period ranging from a few applications to at least one daily application over several months). Preferably desensitization includes the alleviation of allergic symptoms upon administration of the dose. Clinical allergy symptoms include rhinitis, conjunctivitis, asthma, urticaria, eczema, which includes reactions in the skin, eyes, nose, upper and lower airways with common symptoms such as redness and itching of eyes and nose, itching and runny nose, coaching, weezing, shortness of breathe, itching, and swelling of tissue.

"Uniformity of content" as used herein refers to the variation of the doses unit from the stated dose.

"Water content" as used herein refers to the content of residual water in a solid dosage unit determined quantitatively using the Karl Fischer titration principle. This method is based on the principle that a given amount of $I_2$ leads to a transformation of an equivalent amount of water (European Pharmacopoeia (EP) $3^{rd}$ edition, 2.5.12).

As used herein "Water activity $a_w$" is the effective water in a sample. Water activity measurements are carried out using methods known to the person skilled in the art, for example chilled minor dew point technology, relative humidity with sensors that change electrical resistance or capacitance or using a lithium chloride electrode:

$a_w$ can be calculated according to the following equation:

$$a_w = p/ps = ERH\ (\%)/100$$

where
p=partial pressure of water vapor at the surface of the product
ps=saturation pressure, or the partial pressure of water vapor above pure water at the product temperature.
ERH=equilibrium relative humidity.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value.

It has now surprisingly been found that solid dosage form according to the invention provides an oromucosal pharmaceutical allergen product, which provides effective allergen doses giving an allergen specific immune response in a dose-response manner and having acceptable side effects.

It has further been found that it is indeed possible to manufacture a non-compressed fast-dispersing solid dosage form with low friability containing allergens, which is sufficiently robust and does not release hazardous amounts of residue upon handling by the patient.

Moreover, it has surprisingly been found that these formulations are stable at room temperature.

Allergens are in a varying degree particularly susceptible to degradation in an aqueous environment, such as in an aqueous allergen solution or in a product with high water content and/or high water activity.

The European Pharmacopoeia monograph for Allergen Products and "Note for guidance on allergen products", CPMP (London 13, March 1996) state that the moisture levels should not exceed 5% for freeze-dried products (i.e. allergen extracts in vials), and that these should be stored frozen (−20° C.). Cold storage (2-8° C.) is also a requirement for liquid-based sublingual formulations, which further have a limited shelf life. It has surprisingly been found that allergens including labile allergens are stable at room temperature conditions. Even the dosage forms according to the invention having water content above the prescribed maximum level of 5% are stable at room temperature. Without being bound to theory, this may be explained by the fact that the excipients of the fast-dispersing solid dosage form bind the remaining water in the dosage form and reduces the water activity of the allergen solid dosage form. Hence, by reducing the water activity of the formulation, it is possible to obtain a stable formulation with no degradation of the allergen, even though the water content is higher than the maximum level of 5% that is prescribed for allergen extracts in vials.

Water activity is one important factor contributing to the shelf life of a product. It is well known that the water activity of a product affects growth of bacteria as well as the stability, the potency and consistency of pharmaceuticals. Also protein stability is influenced significantly by water activity due to the relatively fragile nature of proteins. Most proteins must maintain conformation to remain active. Maintaining low water activity levels helps to prevent or entice conformational changes, which subsequently is important to ensure that a protein in the form of an allergen is stable. Also hydrolytic degradation of proteins, whether caused by enzymes or not, is affected by the water activity.

Further it is believed that the water content will affect the mechanical strength of the solid dosage forms. In general, high values will increase the risk of the solid dosage form becoming more deliquescent, whereas lower value will affect the robustness of the solid dosage form, e.g. the solid dosage becoming more friable and brittle.

Water activity measurements are carried out by using methods known to the person skilled in the art for example chilled minor dew point technology, relative humidity with sensors that change electrical resistance or capacitance or using a lithium chloride electrode.

The water activity of a solid dosage form preferable does not exceed 0.70 and preferably is between 0.1-0.7, more preferably is between 0.2-0.6, more preferably is between 0.3-0.5, and most preferably is between 0.4-0.5.

The water content of a solid dosage form determined according to the method described in Example 1 preferably does not exceed 25% and preferably is between 0.1%-20%, more preferably is between 0.5-15%, more preferably is between 2-8%, more preferably is between 4-7%, most preferably between 4.5-6% water.

According to one embodiment of the invention an allergen pharmaceutical product is provided in a fast-dispersing solid dosage form, which rapidly dissolves in the oral cavity on contact with saliva, hence bringing the allergen in close contact with the immunological relevant tissue of the mucosa and allowing the allergen to address these. Examples of naturally occurring allergens include pollen allergens (tree, herb, weed, and grass pollen allergens), insect allergens (inhalant, saliva and venom allergens, e.g. mite allergens, cockroach and midges allergens, hymenoptera venom allergens), animal hair and dander allergens (from e.g. dog, cat, horse, rat, mouse, etc.), and food allergens. Important pollen allergens from trees, grasses and herbs are such originating from the taxonomic orders of Fagales, Oleales, Pinales and Platanaceae including for example birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including for example grasses of the genera *Lolium*, *Phleum*, Poa, *Cynodon*, *Dactylis*, *Holcus*, *Phalaris*, *Secale*, and Sorghum, the orders of Asterales and Urticales including for example herbs of the genera *Ambrosia*, *Artemisia*, and *Parietaria*. Other important inhalation allergens are those from house dust mites of the genus *Dermatophagoides* and *Euroglyphus*, storage mite e.g. *Lepidoglyphys*, *Glycyphagus* and *Tyrophagus*, those from cockroaches, midges and fleas e.g. *Blatella*, *Periplaneta*, *Chironomus* and *Ctenocepphalides*, and those from mammals such as cat (genus *Felis*), dog (genus *Canis*), cow (genus Bos) and horse (genus *Equus*), venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi are, for example, those originating from the genera *Alternaria* and *Cladosporium*.

In a more preferred embodiment of the invention the allergen is Bet v 1, Aln g 1, Cor a 1 and Car b 1, Que a 1, Cry j 1, Cry j 2, Cup a 1, Cup s 1, Jun a 1, Jun a 2, jun a 3, Ole e 1, Lig v 1, Pla l 1, Pla a 2, Amb a 1, Amb a 2, Amb t 5, Art v 1, Art v 2 Par j 1, Par j 2, Par j 3, Sal k 1, Ave e 1, Cyn d 1, Cyn d 7, Dac g 1, Fes p 1, Hol l 1, Lol p 1 and 5, Pha a 1, Pas n 1, Phl p 1, Phl p 5, Phl p 6, Poa p 1, Poa p 5, Sec c 1, Sec c 5, Sor h 1, Der f 1, Der f 2, Der p 1, Der p 2, Der p 7, Der m 1, Eur m 2, Gly d 1, Lep d 2, Blo t 1, Tyr p 2, Bla g 1, Bla g 2, Per a 1, Fel d 1, Can f 1, Can f 2, Bos d 2, Equ c 1, Equ c 2, Equ c 3, Mus m 1, Rat n 1, Apis m 1, Api m 2, Ves v 1, Ves v 2, Ves v 5, Dol m 1, Dol m 2, Dol m 5, Pol a 1, Pol a 2, Pol a 5, Sol i 1, Sol i 2, Sol i 3 and Sol i 4, Alt a 1, Cla h 1, Asp f 1, Bos d 4, Mal d 1, Gly m 1, Gly m 2, Gly m 3, Ara h 1, Ara h 2, Ara h 3, Ara h 4, Ara h 5 or shufflant hybrids from Molecular Breeding (Maxygen, Inc.) of any of these.

In the most preferred embodiment of the invention the allergen is grass pollen allergen or a dust mite allergen or a ragweed allergen or a cedar pollen or a cat allergen or birch allergen.

In yet another embodiment of the invention the fast-dispersing solid dosage form comprises at least two different types of allergens either originating from the same allergenic source or originating from different allergenic sources. For example the fast-dispersing solid dosage form comprises grass group 1, grass group 2/3, grass group 5 and grass group 6 allergens or mite group 1 and group 2 allergens from different mite and grass species respectively, weed antigens like short and giant ragweed allergens, different fungi allergens like *alternaria* and *cladosporium*, tree allergens like birch, hazel, hornbeam, oak and alder allergens, food allergens like peanut, soybean and milk allergens.

The allergen incorporated into the fast-dispersing solid dosage form may be in the form of an extract, a purified allergen, a modified allergen, a recombinant allergen or a mutant of a recombinant allergen. An allergenic extract may naturally contain one or more isoforms of the same allergen, whereas a recombinant allergen typically only represents one isoform of an allergen. In a preferred embodiment the allergen is in the form of an extract. In another preferred embodiment the allergen is a recombinant allergen. In a further preferred embodiment the allergen is a naturally occurring low IgE-binding mutant or a recombinant low IgE-binding mutant.

Allergens may be present in equi-molar amounts or the ratio of the allergens present may vary preferably up to 1:20.

In a further embodiment of the invention the low IgE binding allergen is an allergen according to WO 99/47680 or WO 02/40676 or PCT/DK03/00322 ("Allergen mutants").

Several laboratory tests are available for characterising an allergen. The most widely used techniques are sodium dodecyl sulphate polyacrylamide gel electrophoresis (SDS-PAGE), isoelectric focusing (IEF), crossed immunoelectrophoresis (CIE) and Rocket Immuno Electrophoresis (RIE). The quantification of individual allergens may be performed by a variety of quantitative immunoelectrophoretic techniques (QIE), Radial Immune Diffusion (RIE) or by enzyme-linked immunosorbent assays (ELISA). The determination of total allergenic activity is most frequently performed by radio allergosorbent test (RAST), Magic Lite assay (LIA) or related techniques. ELISA-based techniques may also be used.

Guidance to the normally applied, acceptable tests measuring biopotency are found e.g. in Note for Guidance on Allergen Product; The European Agency for the Evaluation of Medicinal Product, CPMP_BWP_243_96, London, 1996.

The classification of an allergen as a major allergen can be subject to several tests. An allergen is commonly classified as a major allergen if at least 25% of the patients shows strong IgE binding (score 3) and at least moderate binding (score 2) from 50% of the patients, the binding being determined by an CRIE (Crossed Radio Immune Electrophoresis) (CRIE Strong binding, i.e. visible IgE-binding on an X-ray film after one day; CRIE Moderate binding, i.e. binding after 3 days; CRIE Weak binding, i.e. binding after 10 days). Strong IgE binding from at least 10% of the patients classifies the allergen as an Intermediate allergen and clearly specific binding from less than 10% of the patients classifies it as a Minor allergen. Other methods may also be used in determining the IgE binding of for instance IgE-blots.

In classical incremental dosage desensitisation, where the dose of allergen in the form of a fast-dispersing solid dosage form is increased to a certain maximum, the preferred potency of a unit dose of the dosage form is from 150-1,000,000 SQ-U/dosage form, more preferred the potency is from 500-500,000 SQ-U/dosage form, more preferred the potency is from 500-375,000 SQ-U/dosage form, more preferably the potency is from 2500-375,000 SQ-U/dosage form, more preferred the potency is from 2500-250,000 SQ-U/dosage form, more preferred 25,000-250,000 SQ-U/dosage form, more preferably 25,000-125,000 SQ-U/dosage form, more preferred 25,000-100,000 SQ-U/dosage form and most preferable 25,000-75,000 SQ-U/dosage form.

In another embodiment of the invention the solid dosage form is a repeated mono-dose, preferably within the range of from 2500-375,000 SQ-U/dosage form, more preferably 2500-250,000 SQ-U/dosage form, more preferably 25,000-250,000 SQ-U/dosage form, more preferably from 25,000-125,000 SQ-U/dosage, even more preferably from 25,000-100,000 SQ-U/dosage form, and most preferably from 25,000-75,000 SQ-U/dosage form.

In a particular preferred embodiment the solid dosage from comprises an grass allergen extract wherein the potency is from 150-1,000,000 SQ-U/dosage form, more preferred the potency is from 500-500,000 SQ-U/dosage form, more preferred the potency is from 500-375,000 SQ-U/dosage form, more preferably the potency is from 2500-375,000 SQ-U/dosage form, more preferred the potency is from 2500-250,000 SQ-U/dosage form, more preferred 25,000-250,000 SQ-U/dosage form, more preferably 25,000-125,000 SQ-U/dosage form, more preferred 25,000-100,000 SQ-U/dosage form and most preferable 25,000-75,000 SQ-U/dosage form.

In yet a further embodiment the potency of a solid dosage form according to the invention is from about 5-50,000 BAU/dosage form, more preferred the potency is from 15-25,000 BAU/dosage form, more preferably the potency is from about 15-17,600 BAU/dosage form, more preferably the potency is from about 65-17,600 BAU/dosage form, more preferably the potency is from about 65-15,000 BAU/dosage form, more preferably the potency is from about 650-15,000 BAU/dosage form, more preferred 650-6,000 BAU/dosage form, more preferred 650-4,700 BAU/dosage form, most preferable 650-3,500 BAU/dosage form.

In another embodiment of the invention the solid dosage form is a repeated mono-dose, preferably within the range of about 65-17,600 BAU/dosage form, more preferably about 65-15,000 BAU/dosage form, more preferably about 650-15,000 BAU/dosage form, more preferred 650-6,000 BAU/dosage form, even more preferred 650-4,700 BAU/dosage form, most preferable 650-3,500 BAU/dosage form.

In a particular preferred embodiment the solid dosage from comprises an grass allergen extract wherein the potency is from about 5-50,000 BAU/dosage form, more preferred the potency is from 15-25,000 BAU/dosage form, more preferably the potency is from about 15-17,600 BAU/dosage form, more preferably the potency is from about 65-17,600 BAU/dosage form, more preferably the potency is from about 65-15,000 BAU/dosage form, more preferably the potency is from about 650-15,000 BAU/dosage form, more preferred 650-6,000 BAU/dosage form, more preferred 650-4,700 BAU/dosage form, most preferable 650-3,500 BAU/dosage form 1 mg allergen extract normally contains between 100,000 and 1,000,000 SQ-unit. This means that 1,000,000 SQ are contained in from 1 mg extract to 10 mg allergen extract, and that 100,000 SQ are contained in from 0.1 mg extract to 1 mg allergen extract. In a similar manner, any SQ dose may be transformed into an allergen extract dose range. On this basis, the above dose ranges given in SQ may be recalculated into dose ranges in mg or µg allergen extract, wherein for the lower SQ limit of a range, the lower limit of the corresponding allergen extract range is used, and wherein for the upper SQ limit of a range, the upper limit of the corresponding allergen extract range is used.

Thus, in a further embodiment a solid dosage form according to the invention has an allergen extract content of about 0.15 µg-10 mg/dosage form, more preferred an allergen extract content of about 0.5 µg-5 mg/dosage form, more preferably an allergen extract content of about 0.5 µg-3.75 mg/dosage form, more preferably an allergen extract content of about 2.5 µg-3.75 mg/dosage form, more preferably an allergen extract content of about 2.5 µg-2.5 mg/dosage form, more preferably an allergen extract content of about 25 µg-2.5 mg/dosage form, more preferred about 25 µg-1.25 mg/dosage form, even more preferred about 25 µg-1 mg/dosage form, most preferable about 25 µg-0.75 mg/dosage form.

In another embodiment of the invention the solid dosage form is a repeated mono-dose, preferably within the range of about 2.5 µg-3.75 mg/dosage form, more preferably 2.5 µg-2.5 mg/dosage form, more preferably of about 25 µg-2.5 mg/dosage form, more preferred of about 1.5 µg-1.25 mg/dosage form, even more of about preferred 25 µg-1 mg/dosage form, most preferable of about 25 µg-0.75 mg/dosage form.

In a further embodiment, a solid dosage form according to the invention has a major allergen content of about 0.015 µg-1 mg/dosage form, more preferred of about 0.05 µg-500 µg/dosage form, more preferably of about 0.05 µg-375 µg/dosage form, more preferably of about 0.25 µg-375 µg/dosage form, more preferably of about 0.25 µg-250 µg/dosage form, more preferably of about 2.5 µg-250 µg/dosage form, more preferred about 2.5 µg-125 µg/dosage form, even more preferred about 2.5 µg-100 µg/dosage form, most preferable about 2.5 µg-75 µg/dosage form.

In another embodiment of the invention the solid dosage form is a repeated mono-dose, preferably within the range of 0.25 µg-375 µg/dosage form, more preferably of about 0.25 µg-250 µg/dosage form, more preferably of about 2.5 µg-250 µg/dosage form, more preferred about 2.5 µg-125 µg/dosage form, even more preferred about 2.5 µg-100 µg/dosage form, most preferable about 2.5 µg-75 µg/dosage form.

The content of major allergens may be accounted for by several major allergens depending on the allergen source in question. Normally the number of major allergens is in the range of 1-10, mostly 1-5.

The major allergen may be comprised in an allergen extract or be recombinantly produced. Recombinant major allergens may be used in the same amount as in allergen extracts comprising such major allergen or in higher doses. Higher doses are believed to be more effective, but are also believed to be associated with a risk of potentially more frequent or more severe side effects.

In a further preferred embodiment major allergens include grass group 1 allergen e.g. phl p 1, lol p 1, sor h 1, dac g 1, cyn d 1, hol l 1, pha a 1, grass group 2/3 allergen e.g. phl p 2/3, lol p 2/3, grass group 5 allergen e.g. phl p 5, lol p 5, dac g 5, poa p 5, grass group 6 allergen e.g. phl p 6, poa p 6, tree pollen group 1 allergen e.g. bet v1, aln g 1, cor a 1, car b 1, mite group 1 allergen e.g. der p 1, der f 1, eur m 1, mite group 2 allergen e.g. der p 2, der f 2, eur m2, cat allergen e.g. fel d 1, cedar group 1 and group 2 allergen e.g. cry j 1, cry j 2, short or giant ragweed pollen allergen e.g. amb a 1, amb a 2, amb l 1, amb t 2.

A dose response effect is found cf. example 6 for solid allergen dosage forms administered oromucosally. As allergic individuals are an inhomogeneous group displaying different symptoms and different degrees of severity of their symptoms when exposed to even the same allergen, effective doses may vary. Some patients can tolerate larger doses without experiencing unacceptable side effects, while others are hypersensitive. In some cases escalating doses may be given to reach high dose levels as it is generally believed that larger doses are believed to be more effective doses. It is believed that for the majority of the average allergic population an effective dose of allergen according to the invention will preferably be between 65 BAU/solid dosage form-17,600 BAU/solid dosage form, but a dose as low as 4 and up to 47,000 BAU may be applicable for other allergic patients. Equally hereto, a dose of allergen extract of 0.5 µg-3.75 mg/dosage form, or a dose with a major allergen content of 0.05 µg-375 µg/dosage form may be suitable for an average allergic individual.

For hypoallergenic variants of major allergens, i.e. allergens with a decreased ability to caused immediate or late phase allergic reactions, a dosage form according to the invention preferably contains 10-100 times more major allergen per dosage form. Such hypoallergenic variants may be of recombinant or natural origin.

The allergen content of a solid dosage form according to the invention can be determined by routine immune assays such as CIE (Cross Immune Electrophoresis), RIE (Radio Immune Electrophoresis) and SDS-PAGE (Sodium Dodecyl Sulphate Poly Acrylamide Gel Electrophoresis) and immune assays such as ELISA and Magic Like Specific IgE assay (LIA) against extract components such as major allergens.

In order to ensure a sufficient shelf life for the final product, dosage forms which do not significantly change after manufacture with respect to physical and chemical properties, e.g. potency and content of the allergen, mechanical robustness and organoleptical properties, are preferred.

For the purpose of this invention the stability of the active ingredient, i.e. the allergen, is assessed by means of major allergen content. Further to that stability is preferably also assessed by means of potency measurements of the allergen such as total allergen activity.

The "initial allergenic activity" or the "initial content of at least one major allergen" of a solid dosage form means the value of the "allergenic activity" or the "content of at least one major allergen" in the final dosage form after the manufacturing process has ended.

The "theoretical allergenic activity" or the "theoretical content of at least one major allergen" of a solid dosage form means the value of the "allergenic activity" or the "content of at least one major allergen" of a dose of the added allergen, e.g. in the form of an extract, before being formulated into a solid dosage form.

Loss in the allergen content of at least one major allergen is preferably less than 50% of the total initial content, more preferably less than 30% of the total initial content, more preferably less than 20% of the total initial content, more preferably less than 15% of the initial content, more preferably less than 10% of the initial content, more preferably less than 5% of the initial content, more preferably less than 2% of the initial content.

Further loss in total allergen activity according the method described in Example 1 should preferably be less than 50% of the total initial activity, more preferably less than 30% of the total initial activity, more preferably less than 20% of the total initial activity, more preferably less than 15% of the total initial activity.

Normally, stability testing is conducted according to the current guidelines by ICH (e.g. ICH guideline ICQ/Q1AR2 (Adopted by CPMP, March 2003, issued as CPMP/ICH/2736/99)) and FDA. Conditions for stability testing are often referred to as zone 1-4 conditions. Zone 1 and 2 represent climatic conditions in EC, Japan and US. Normally, solid dosage forms according to the present invention in their final container should preferable be stable for a least 3 months, more preferably for at least 6 months, more preferably for at least 12 months, even more preferred for at least 18 months, most preferred at least for 2 years at "long term" conditions 25° C./60 RH, more preferable at intermediate condition 30° C./65 RH, even more preferable at "accelerated conditions" 40° C./75 RH.

To ensure that the solid dosage form is sufficiently robust during storage and when handled by the patient, the dosage form needs to have a certain resistance to external force, but at the same time the solid dosage form needs to disintegrate quickly in the mouth.

Thus, further to the stability of the active ingredient i.e. the allergen solid dosage forms can also be assessed by additional parameters, such as mechanical robustness like friability, tensile strength, and peak load to fracture. In addition, the stability of the solid dosage forms can be assessed by physical properties such as the dispersion time and organoleptical properties like visual appearance of the dosage form.

These parameters can be evaluated by e.g. measurements of Peak load to fracture or tensile strength of the solid dosage forms of the current invention. As it is apparent from the equation from which the tensile strength can be calculated, the tensile strength value obtained depends on a number of parameter, which are subject to variation. For example, thickness or the diameter of the solid dosage form will contribute to the variation of value. Therefore, Peak load to fracture is believed to be an even more accurate parameter for evaluation of the robustness of the solid dosage units of the current invention.

In an embodiment the solid dosage form has a Peak load to Fracture not less than 0.05 Kgf and below 0.9 KgF. Preferred are dosage forms which have a Peak load to Fracture which is between 0.05-0.9 KgF, more preferred between, 0.1-0.8 KgF, most preferred between 0.1-0.6 KgF.

In a further embodiment of the current invention the solid dosage form has a tensile strength less than 1.0 N/mm2, more preferred below 0.9 N/mm2.

Preferably fast-dispersing dosage form disintegrates instantaneously or quickly in the mouth upon contact with the saliva in order to ensure maximum exposure of allergen to immune competent tissue of the mucosa before swallowing. In a preferred embodiment the solid dosage form disintegrates in less than about 90 seconds, preferably in less than about 60 seconds, preferably in less than about 30 seconds, more preferably in less than about 20, more preferably in less than about 15 seconds, even more preferably in less than about 10 seconds in the oral cavity, even more preferably in less than about 5 seconds, most preferably in less than about 2 seconds in the oral cavity.

In a preferred embodiment of the invention, the compositions of the invention are fast-dispersing solid dosage forms comprising a solid network of the allergen and any water-soluble or water-dispersible matrix. The network is obtained by subliming solvent from a composition in the solid state, the composition comprising a solution of the allergen and the matrix. More preferably the network is obtained by lyophilization.

Pharmaceutically acceptable excipients forming part of the matrix in the fast-dispersing solid dosage form according to invention are matrix forming agents and additionally other suitable excipients such as antacids, diluents, enhancers, mucoadhesive agents, flavouring agents, taste masking agents, preservatives, antioxidants, surfactants, viscosity enhancers, colouring agents, pH modifiers, sweeteners etc. These excipients are all selected in accordance with conventional pharmaceutical practice in a manner understood by persons skilled in the art of formulating allergen therapeutics.

Matrix forming agents suitable for use according to the present invention include excipients derived from animal or vegetable proteins such as gelatines, dextrins and soy, wheat and *psyllium* seed proteins; gums such as acacia, guar, agar and xanthan; polysaccharides; starch and modified starch, alignates; carboxymethylcellulose; carrageenans; dextrans; pectins; synthetic polymers such as polyvinylpyrrolidone; and polypeptide/protein or polysaccharide complexes such as gelatine-acacia complexes. Gelatines are a heterogeneous mixture of water soluble colloid macromolecules. Such heterogeneous mixtures of average molecular weights distribution may be obtained from hydrolytic action on collagen rich material of animal origin such as bone, skin, tendons, ligaments etc. Gelatines may be derived from mammal e.g. cattle, pig or non-mammals e.g. warm or cold-water fish. Gelatines can be hydrolysed or non-hydrolysed, cross-linked or non-cross-linked. They can further be of a gelling or non-gelling type, the non-gelling type typically being derived from coldwater fish. In another particular embodiment starch is used. Starches are complex mixtures of carbohydrate polymers.

Other matrix forming agents suitable for use according to the present invention include sugars such as mannitol, dextrose, lactose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

The solid dosage form preferably comprises at least about 50% W/W of at least one matrix forming agent of the dosing solution. The term "dosing solution" as used in this context means a non-solid volume of a formulation of the matrix forming agents, the allergen and other optional excipients that is prepared before the solidification step.

In one embodiment of the invention the dosing solution for forming the solid dosage form comprises about 5-30% W/W, more preferably about 5-20% W/W, even more preferred between about 5-12% W/W of at least one matrix forming agent.

The need for dry matter content of the dosing solution will also depend on the dimensions of the tablet. Preferably the solid dosage forms according to the present invention have a diameter between about 3 to about 30 mm, more preferably between about 5 to about 20 mm. Preferably the solid dosage forms according to the present invention have a weight between about 1 to about 100 mg, more preferably between about 10 to about 50 mg, most preferably between about 25 to about 35 mg. Preferably the solid dosage forms according to the invention have a height between about 0.5 to about 7.5 mm, more preferably between about 1 to about 5 mm.

A fast-dispersing solid dosage form comprising fish gelatine and mannitol as matrix-forming excipients has been found to be especially advantageous with respect to stability, visual appearance, low friability, tensile strength, peak load to fracture and mouth feel. In a preferred embodiment the fast-dispersing solid dosage forms comprises a solid network of the allergen and matrix form agents in the form of fish gelatine and mannitol. In order to obtain a solid network, the ratio of fish gelatine to mannitol should be controlled. In a preferred embodiment the ratio of fish gelatine to mannitol is from about 2:20 to about 20:1, more preferably from about 2:10 to about 10:1, most preferably from about 3:5.5 to about 6.5:3.

In yet a further embodiment the ratio of fish gelatine to mannitol is 4:3.

In another embodiment the ratio of fish gelatine to mannitol is 6.5:5.5.

In a further embodiment the ratio of fish gelatine to mannitol is 6.0:5.08.

The solid dosage form according to the present invention may be manufactured from a dosing solution, which is first frozen and then freeze dried. In a preferred embodiment the content of fish gelatine is between about 2-20% W/W of the dosing solution and the content of mannitol is between about 1-20% W/W of the dosing solution. In another preferred embodiment the content of fish gelatine is between about 2-10% W/W of the dosing solution and the content of mannitol is between about 1-10% W/W of the dosing solution. In a further preferred embodiment the content of fish gelatine is between about 3-6.5% W/W of the dosing solution and the mannitol is between about 3-5.5% W/W of the dosing solution.

In yet a further embodiment the matrix comprises about 4% W/W of the dosing solution fish gelatine and about 3% mannitol W/W of the dosing solution In another embodiment the matrix comprises about 6.5% W/W fish gelatine of the dosing solution and about 5.5% W/W mannitol of the dosing solution.

In a further embodiment the matrix comprises 6.0% W/W fish gelatine of the dosing solution and 5.08% W/W mannitol of the dosing solution.

A fast-dispersing solid dosage form comprising starch and mannitol as matrix-forming excipients has also been found to be especially advantageous with respect to stability, visual appearance, low friability, tensile strength, peak load to fracture and mouth feel. In a preferred embodiment the fast-dispersing solid dosage forms comprises a solid network of the allergen and matrix form agents in the form of starch preferably pre-gelatinised from e.g. potato, wheat, maize, corn or rice and mannitol. In order to obtain a solid network, the ratio of starch to mannitol should be controlled. In a preferred embodiment the ratio of starch to mannitol is from about 2:20 to about 20:1, more preferably from about 2:10 to about 10:1, most preferably from about 3:5.5 to about 6.5:3.

In yet a further embodiment the ratio of starch to mannitol is 1:1.

The solid dosage form according to the present invention is manufactured from a dosing solution, which is first frozen and then freeze dried. In a preferred embodiment the content of starch is between about 2-20% W/W of the dosing solution and the content of mannitol is between about 1-20% W/W of the dosing solution. In another preferred embodiment the content of starch is between about 2-10% W/W of the dosing solution and the content of mannitol is between about 1-10% W/W of the dosing solution. In yet a further preferred embodiment the content of starch is between about 3-6.5% W/W of the dosing solution and the mannitol is between about 3-5.5% W/W of the dosing solution In another embodiment the matrix comprises about 4.4.% W/W starch of the dosing solution and about 4.4% W/W mannitol of the dosing solution.

Preferably pH is adjusted prior to solidification of the allergen and matrix containing solution to avoid denaturation of the allergen, precipitation and assure a stable product. The optimum pH for different allergens in solution span almost the entire pH range as does their isoelectric point (pI). Mixtures of allergens like extracts equally have optimum pH for solubility and stability determined by factors like the concentration of the individual allergens in the extract. Therefore an individual determination of a feasible range of pH for a formulation according to this invention may be envisaged. The optimum pH for the allergen in question is determined by carrying out accelerated stability studies with formulations with different pH. The design of such studies is known to the person skilled in the art.

Preferably matrix compositions containing an allergen extract should be adjusted to pH between 3.5-10, more preferably 4-9, most preferably 6-9.

Furthermore it is well known in the art that ionic strength may be a parameter affecting the stability of a freeze-dried solid dosage form primarily through its effect of the freeze-drying processes. Also it is known that high ionic strengths affect precipitation. Accordingly, an optimum must be established by measurements well known to one skilled in the art. Preferably the ionic strength of an extract of 10 µg/ml is in between 1-1500 µS/cm (S=Simens), more preferably between 300-800 µS/cm, most preferably about 500 µS/cm, for a matrix and allergen containing system it is preferred that the ionic strength is between 1-2000 µS/cm, more preferably about 500-1500 µS/cm.

Solid dosage forms according to the invention may further comprise colouring agents, flavours, pH modifiers or taste-masking agents. Suitable colouring agents include red, black and yellow iron oxides and FD & C dyes such as FD & C blue No. 2 and FD & C red No. 40. Suitable flavouring agents include mint, raspberry, liquorice, orange, lemon, grapefruit, caramel, vanilla, cherry and grape flavours and combination of these. Suitable pH modifiers include citric acid, tartaric acid, phosphoric acid, hydrochloric acid and maleic acid. Suitable sweeteners include aspartame, acesulfame K and thaumatic. Suitable taste-masking agents include sodium bicarbonate, ion-exchange resins, cyclodextrin inclusion compounds, adsorbates or microencapsulated actives.

Adjuvants are normally used to enhance the absorption of the allergen as well as to enhance the immune-stimulating properties of the allergen.

In another preferred embodiment of the invention the fast-dispersing solid dosage form according to the invention does not comprise an adjuvant.

It has also surprisingly been found that it is not necessary to incorporate an adjuvant into the fast-dispersing solid dosage form in order to enhance the immune-stimulating properties of the allergen in question. That is to say a solid dosage from as described herein can raise a specific immune response as demonstrated in example 6.

In one embodiment of the invention at least one adjuvant is incorporated into the dosage form according to the invention. Examples of suitable adjuvants are aluminium salts, aluminium hydroxide such as Alhydrogel®, non-toxic bacterial fragments, cytokines, cholera toxin (and detoxified fractions thereof), cholera toxin subunit b, chitosan, homologous heat-labile fragments of *E. coli* (and detoxified fractions thereof), saponins, bacterial products such as lipopolysaccharides (LPS) and muramyl dipeptide (MDP), liposomes, CpG (immunostimulatory DNA sequences), lactide/glycolide homo±copolymers in the form of microparticular polymers etc. The use of adjuvants in allergen pharmaceutical product e.g. vaccines are often reasoned by the fact the allergens in question are not able to penetrate the barrier to be passed. The adjuvants thus may serve as absorption enhancing agents or they may act as immunostimulants. The use of adjuvants may, however, be associated with serious draw backs such as unintended stimulation of various mechanisms of the immune response, systemic lupus erythematosus or affecting the barrier capabilities of the mucosal membranes and thus allowing the passage of hazardous substances. Further from an industrial point of view addition of an adjuvant further constitute further manufacturing and material cost besides the large demand for documentation in respect to drug registration.

A non-compressed fast-dispersing solid dosage form may be mucoadhesive to some extent. However in a preferred embodiment of the invention, it may be necessary to further add mucoadhesive excipients to said dosage form in order to increase the contact time of the dosage form with the mucosa of the oral cavity. Suitable mucoadhesive excipients are polyacrylic polymers such as carbomer and carbomer derivatives; cellulose derivatives such as hydroxypropylmethylcellulose, hydroxyethylcellulose, hydroxypropylcelllulose and sodium carboxymethylcellulose; natural polymers such as gelatine, sodium alginate, pectin and glycerol.

In further embodiment of the invention the allergen dosage form dissolved in saliva is not swallowed until 3 min after administration in order to allow sufficient contact time for e.g. absorption over the mucosal membrane in the mouth.

In yet a further preferred embodiment the allergen dosage form is not diluted in the oral cavity e.g. by intake of a fluid like water until after 5 min.

Adverse events or side effects are known to exist also in connection with allergy treatment. In particular treatment aiming at modulating an ongoing response in a sensitised individual may pose a risk for inducing side effect upon administration of allergen. Normally side effects seen in connection with oromucosal treatment are reported in the eye, nose, mouth, the upper and lower airway and depending on degree found acceptable. Most common are itching phenomena. Adverse reactions, such as anaphylactic shock, swelling of upper and lower airways, difficulty breathing, blood pressure drop, cardiac arrest would not be acceptable.

The fast-dispersing solid dosage form according to the invention may be manufactured and packed in disposable containers containing a multiplicity of solid dosage forms i.e. multi dosage containers. The methods and materials as described in U.S. Pat. Nos. 5,729,958 and 5,343,762 are particularly favoured. Examples of suitable multi dosage containers are All Aluminium Blister packs, blister packs made of polymers e.g. polypropylene, blister packs of PVC and blister packs formed from PVC/PVdC laminate and sealed with e.g. aluminium laminated to calendered kraft paper, Aclar® or Triplex®.

In an embodiment the fast-dispersing dosage form is manufactured and packed in blister packs formed from PVC/PVdC laminate and sealed with aluminium laminated to calendered kraft paper. In another embodiment hereof the blister pack are enclosed in an aluminium sachet of suitable size, composed of aluminium laminated to calendered kraft paper.

In yet another embodiment the fast-dispersing dosage form is packed in blister packs formed from aluminium and sealed with aluminium laminated to calendered kraft paper.

In a further embodiment the fast-dispersing dosage form is packed in multilamilar blister packs formed from e.g. five layer aluminium laminate and sealed with aluminium laminated to calendered kraft paper.

In yet another embodiment the fast-dispersing dosage form is packed in blister packs formed from aluminium laminate and sealed with aluminium laminated to calendered kraft paper in such a way that is difficult for children to open the blister pack e.g. child resistant packs.

A solid dosage form of this type generally may be characterized by a low mechanical strength compared to compressed tablets, because of the inherent nature of such a non-compressed dosage form. This may result in the release of residual particles containing the allergen on removal from the blister pocket and during handling of the dosage form by the patient. In most situations this is of no or mainly cosmetic importance. However, this is especially detrimental when the active ingredient is an allergen, because low amounts allergen can elicit an allergic reaction in a disposed person or sensitise a previously non-sensitized individual. Normally exposure is in the range of 10 µg/year to major allergen protein accumulated for e.g. pollen allergens or dust mite allergens, which is adequate to give sensitisation or symptoms.

Upon handling the solid dosage forms, allergens may come in contact with target organs like the airways or the eye and elicit a response in an allergic person. One dosage form may contain as much allergen as a person is exposed to over one year or more depending upon the nature of the exposure. It is possible to induce eye symptoms in allergic patients using a conjunctival allergen challenge. Based on such challenge studies it can be estimated how much allergen extract is needed to induce conjunctival symptoms. In a population of patients with severe grass-pollen induced hayfever, the lowest dose of grass pollen extract causing conjunctival symptoms was proposed to be 3000 SQ-U/ml× 0.05 ml=150 SQ-U (median value) (S. R. Durham, S. M. Walker, E. M. Varga, M. R. Jacobson, F. O'Brien, W. Noble, S. J. Till, Q. A. Hamid, and K. T. Nouri-Aria. Long-term clinical efficacy of grass-pollen immunotherapy. N. Engl. J. Med. 341 (7):468-475, 1999).

In order to ensure that allergen containing residues from the solid dosage form is not released to the environment upon opening the multi dosage container, it is important that the friability of the dosage form is as low as possible without jeopardising the allergen release from the dosage form following oral administration.

Thus, in one embodiment less than about 500 SQ-U may be released from each solid dosage form during manual handling, more preferably less than about 250 SQ-U, more preferably less than about 150 SQ-U, more preferably less than about 75 SQ-U, more preferably less than about 25 SQ-U, most preferably less than about 10 SQ-U.

In another embodiment less than about 13 BAU may be released from each solid dosage form during manual handling, more preferably less than about 7 BAU, most preferably less than about 5 BAU, more preferably less than about 1.95 BAU, more preferably less than about 0.65 BAU, and most preferably less than about 0.26 BAU.

In a further embodiment less than about 0.5 µg allergen extract may be released from each solid dosage form during manual handling, more preferably less than about 0.25 µg allergen extract, most preferably less than about 0.15 µg allergen extract, more preferably less than about 0.075 µg allergen extract, more preferably less than about 0.025 µg allergen extract, and most preferably less than about 0.01 µg allergen extract.

In yet another embodiment less than about 0.05 µg major allergen may be released from each solid dosage form during manual handling, more preferably less than about 0.025 µg major allergen, most preferably less than about 0.015 µg major allergen, more preferably less than about 0.0075 µg major allergen, more preferably less than about 0.0025 µg major allergen, most preferably less than about 0.001 µg major allergen.

In a preferred embodiment of the present invention the residual content of dust in the multi dosage container after removing the dosage form do not exceed about 2% of total allergen content, more preferred about 0.5% of total allergen content of a solid dosage form and more preferably about 0.2% of total allergen content of a solid dosage form and most preferably about 0.1% of total allergen content of a solid dosage form, more preferably about 0.01%, more preferred about 0.005%, more preferred about 0.003% of total allergen content of a solid dosage form, most preferred about 0.001% of the total allergen content of a solid dosage form.

As used herein "friability test" shall refer to any suitable test that measures the ease with which a solid dosage form crumbles, falls to pieces, are reduced to powder. Suitable friability test to use in the current invention are illustrated below and include European Pharmacopoeia 3rd edition (EP 3rd ed.) Pharmaceutical technical procedures 2.9.7. Normally friability testing of tablets is performed as set out in the EP 3rd ed. 2.9.7. and USP <1216>, wherein loss of weight is assessed as a parameter of an intact dosage form. The EP 3rd ed. 2.9.7. friability test uses a drum having a diameter of 286 mm and about 39 mm in depth. A sample of the tablets are placed on a sieve no. 100 and any loose residuals are removed by use of air pressure or a soft brush. The tablets are weighed and thereafter placed in the drum. The tablets are rotated for 100 times in the drum. Loose residuals are then removed as just described and the tablets are weighed again. The result is then expressed as the loss of mass and is calculated as a percentage of the initial mass. According to USP <1216> a drum with a diameter between 283 and 291 and a depth between 36 and 40 mm may be used and a rotation of 25±1 rpm. Accordingly, the intactness of the current dosage form may be assessed by visual inspection and measurement of tablet weight upon having been subject to such a method. Alternatively, due to the low weight of dosage forms according to the invention the weighing can be replaced with an immune assay specific for the allergen in question.

The use of a modified friability test has been found to be a useful tool in assessing which compositions are most stable with respect to robustness and mechanical strength.

In an embodiment the friability of said solid dosage form measured as the amount of allergen released is less than about 500 SQ-U per solid dosage form, more preferably less than about 250 SQ-U per solid dosage form, more preferably less than about 150 SQ-U per solid dosage form, more preferably less than about 75 SQ-U per solid dosage form, more preferably less than about 50 SQ-U per solid dosage form, more preferably less than about 25 SQ-U per solid dosage form, most preferably less than about 10 SQ-U per solid dosage form in any suitable friability test that exerts a sufficient external force on the compositions to be tested.

In a more preferred embodiment the friability measured as the amount of allergen released is less than about 500 SQ-U per solid dosage form, more preferably less than about 250 SQ-U per solid dosage form, more preferably less than about 150 SQ-U per solid dosage form, more preferably less than about 75 SQ-U per solid dosage form, more preferably less than about 50 SQ-U per solid dosage form, and more preferably less than about 25 SQ-U per solid dosage form, most preferably less than about 10 SQ-U per solid dosage form in a friability test performed according to the Pharmacopoeia EP 3$^{rd}$ ed.

In an even more preferred embodiment the friability measured as the amount of allergen released is less than 500 SQ-U per solid dosage form, more preferably less than 250 SQ-U per solid dosage form, more preferably less than about 150 SQ-U per solid dosage form, more preferably less than about 75 SQ-U per solid dosage form, more preferably less than about 50 SQ-U per solid dosage form, and more preferably less than about 25 SQ-U per solid dosage form, most preferably less than about 10 SQ-U per solid dosage form in an method comprising the following steps;
  (a) placing individual sealed blisters each containing a solid dosage form in equipment suitable for friability measurements;
  (b) moving the sealed blister contaning the solid dosage form for an appropriate time and at an appropriate velocity;
  (c) removing the sealed blister containing the solid dosage form;
  (d) opening the blister and placing the solid dosage form and any residues in a container;
  (e) removing the solid dosage form unit from the container leaving any loose residuals in said container;
  (f) performing an allergen specific assay on said residues determining the allergen content in said residues; and
  (g) optionally calculating the percentage allergen content in said residues of the total allergen content of the solid dosage form unit.

In another embodiment the friability of said solid dosage form measured as the amount of allergen released is less about 0.5 μg allergen extract per solid dosage form during manual handling, more preferably less than about 0.25 μg allergen extract per solid dosage form, more preferably less than about 0.15 μg allergen extract per solid dosage form, more preferably less than about 0.075 μg allergen extract per solid dosage form, more preferably less than about 0.025 μg allergen extract per solid dosage form, most preferably less than about 0.01 μg allergen extract per solid dosage form in an method comprising the following steps;
  (a) placing individual sealed blisters each containing a solid dosage form in equipment suitable for friability measurements;
  (b) moving the sealed blister contaning the solid dosage form for an appropriate time and at an appropriate velocity;
  (c) removing the sealed blister containing the solid dosage form;
  (d) opening the blister and placing the solid dosage form and any residues in a container;
  (e) removing the solid dosage form unit from the container leaving any loose residuals in said container;
  (f) performing an allergen specific assay on said residues determining the allergen content in said residues; and
  (g) optionally calculating the percentage allergen extract content in said residues of the total allergen extract content of the solid dosage form unit.

In yet another embodiment the friability measured as the amount of allergen released is less than about 0.05 μg major allergen, more preferably less than about 0.025 μg major allergen, more preferably less than about 0.015 μg major allergen per solid dosage form, more preferably less than about 0.0075 μg major allergen per solid dosage form, more preferably less than about 0.0025 μg major allergen per solid dosage form, most preferably less than about 0.001 μg major allergen per solid dosage form in an method comprising the following steps;
  (a) placing individual sealed blisters each containing a solid dosage form in equipment suitable for friability measurements;
  (b) moving the sealed blister contaning the solid dosage form for an appropriate time and at an appropriate velocity;
  (c) removing the sealed blister containing the solid dosage form;
  (d) opening the blister and placing the solid dosage form and any residues in a container;
  (e) removing the solid dosage form unit from the container leaving any loose residuals in said container;
  (f) performing an allergen specific assay on said residues determining the major allergen content of at least one major allergen in said residues; and
  (g) optionally calculating the percentage of at least said major allergen in said residues of the total major allergen content of the solid dosage form unit.

In another preferred embodiment of the method between 1 and 100 blisters containing the solid dosage form an equipment for friability measurements as described in European Pharmacopoeia V.2.9.7 is used in step a), the solid dosage forms are rotated for 100 turns at 25±1 rpm in step b), and the allergen specific assay is an immunochemical allergen specific assay in step f).

In a further preferred embodiment of the method for measuring friability the allergen content is determined by an ELISA assay.

Furthermore, the oral dosage form must have an appealing appearance. Hence, as a part of the quality control the fast-dispersing solid dosage forms according to the invention are preferably subjected to visual inspection e.g. colour, shape, irregularities and defects.

In order to ensure optimum compliance of the patient, the dosage form may also be tested for mouth feel. For example, the patients perceive the dosage form as being pleasant when it is placed in the mouth and allowed to disintegrate.

As allergens are very bio-potent for the allergic person i.e. even small amount may trigger a response, uniformity of content is an important parameter during treatment to ensure, for example, that a pattern experienced by a patient is reproducible when taking the same dose. Preferably the variation of content of allergen of units within a multi dosage container is within ±10%, preferably within ±7%, most preferable within ±5% compared to the set dose.

A multi dosage container may contain any conceivable number of fast-dispersing solid dosage forms. Preferably solid allergen dosage forms are packaged and used as a group. Individual solid dosage forms are packaged by dispensing as a liquid mixture into individual containers, followed by removal of water. Multiple blisters may be arranged in larger sheets and multiple sheets may be packaged and sold together. For example, a container such as a blister pack may comprise a multiplicity of solid dosage forms preferably 1-100 solid dosage forms, more preferably 1-35, and most preferably 1-10 solid dosage forms per blister pack. Another embodiment provides economy of manufacture, distribution and storage via the use of multiple blister packs that may, for example provided 2, 3, 4, 5, 6 or more for a single intended course of treatment use. This particular packaging scheme particularly is useful for mono-dose treatments, and is made possible by dosing regimens, as described herein, that lack an up-dosing step.

Another embodiment provides a treatment pack for the treatment of allergy or alleviating symptoms of allergy. The treatment pack comprises a sealed package of multiple solid dosage forms, each of which comprises an effective amount of an allergen. The treatment pack may contain for example, at least 2, 4, 6, 7, 10, 14, 30, 60, 90, 100, 120, 200, 240, or more solid dosage forms. The treatment pack may contain enough dosage forms for an entire treatment, or enough for a portion of a treatment. Advantageously the treatment pack contains at least one month's supply of unit doses.

In another advantageous embodiment of the invention, all solid dosage forms of a treatment pack contain the same allergen dosage, thus removing the necessity for manufacturing, distributing, and storing multiple dosage units for treatment of a single allergy in an individual.

A kit comprising a treatment pack may further comprise instructions concerning use of the solid dosage form. The instructions may comprise a warning, dosage regimen instruction, or any other information of value to the user. The instructions physically may comprise, for example, a separate instruction pamphlet, a paper, a placard, and/or one or more notices printed on a container such as a box that holds the unit doses. The instructions also may be supplied as a compact disk or other computer readable medium, or a video cassette.

Most desirably, the multiple solid dosage forms of a treatment pack have been formed from a liquid mixture by an in situ process that removes a suspension and/or solvation liquid, which may comprise water and/or other organic solvents and are fast dispersing.

In another embodiment each of the solid dosage forms of a treatment pack are located in individually sealed blisters in a multiple blister pack.

In a further embodiment the solid dosage forms of a treatment pack comprise gelatine, more preferably fish gelatine.

In yet a further embodiment the solid dosage forms of a treatment pack further comprise mannitol.

In yet another embodiment of a treatment pack the effective amount of solid dosage form is between about 2.5 µg-about 3.75 mg extract/solid dosage form.

Clinical allergy manifestation and symptoms are several and may vary depending on the sensitized individual and the allergy inflicted. Common are symptoms like edema, itching, redness and running of the eyes and nose (rhinitis and conjunctivitis) and symptoms from upper and lower airway like wheezing, coughing, shortness of breath, skin condition like eczema, urticaria and itching. Other symptoms like fatigue are also experienced. Symptomatic treatment aims at reducing or affecting severity of the symptoms or reducing the need for other drugs given in parallel. Symptomatic drug includes antihistamines like $H_1$ and $H_2$ receptor antagonists, intranasal and systemic corticosteroids, non-steroid anti-inflammatory drugs, nasal decongestants like adrenoceptor agonists. Treatment and relief of one or more allergic symptom or the reduction in the need for other medication is a further object of this invention.

Allergy is a widespread disease in mammal including humans and animals such as dogs and horses. Thus, a further object of the invention is to provide a method for treatment of allergy or alleviating symptoms of allergy in mammals comprising oromucosal administration of an effective amount of an allergen vaccine dosage form comprising (a) a matrix, and (b) at least one allergen in any of the above described embodiments.

Treatment of in particular seasonal allergies such as hay fever is normally associated a particular time of year were exposure to the offending allergen is present or elevated. The allergen season is will vary with the allergen source e.g. the pollen and the climatic conditions for the allergen source in the particular territory. Thus, the season for an allergen will differ in one part of the world from another part of the world depending on the climate, but will normally fall within the same period of the year for the same territory varying with the actual conditions of that year (see for instance "Aerobiology and inhalant allergies", Chapter 19, T.A.E. Platts-Mills & W.R. Solomon (Ed. S. Manning) 1993, Mosby-Year Book, St. Louis). This will be well known to a skilled person when a season is normally expected to start for a particular allergen in a particular region.

In one embodiment of the invention a methods of treatment is provided including a pre-seasonal treatment i.e. an administration of solid dosage forms according to the invention before the allergen season. In a particular preferred embodiment the pre-seasonal treatment period comprises administration of solid dosage according to the invention for a period of more than 2 weeks prior to the allergen season, more preferably between 4-20 weeks, most preferably between 8-12 weeks.

Another object of the invention is to provide a method for treatment of allergy or allergic symptoms comprising oromucosal administration of an effective amount of an allergen vaccine dosage form comprising (a) a matrix, and (b) at least one allergen further comprising at least one anti-allergic drug e.g. antihistamines and histamine synthesis inhibitors in any of the above described embodiments. Preferably such anti-allergic drugs include bromapheniramine, cetirizine, fexofenadine, cyproheptadine, dexchlorpheniramine, hydroxizine, ketofene, mequitazine, oxotomide, mizolastine, ebastine, astemizole, carbinoxamide, alimemazine, buclizine, cyclizine, hydrochlorate, doxylamine, tritoqualine.

Also the invention also includes use of a pharmaceutical product comprising a non-compressed, fast dispersing solid dosage form comprising an allergen and at least one matrix forming agent for oromucosal treatment of allergy or alleviation of allergy symptoms.

In yet another embodiment of the invention a pharmaceutical product comprising a stable, fast-dispersing, non-compressed allergen solid dosage form with low friability comprising (a) a matrix, and (b) at least one allergen further comprising an antihistamine is used for oromucosal treatment of allergy or allergic symptoms.

Another embodiment provides a method for treating allergy or alleviating symptoms of allergy, comprising providing a a) treatment pack and b) repeatedly adminstering oromucosally one or more dosage forms of from the treatment pack until symptoms are alleviated.

Also a further embodiment provides a treatment regimen that utilizes a single dose for completing an entire sensitization treatment, without having to updose i.e. increase with different level(s) of allergen till reaching the particular dose. This embodiment is advantageous because it simplifies and economizes on dosage form manufacture, distribution and storage by not requiring multiple dose quantities for a single treatment. Moreover, by simplifying a treatment course, patient compliance is improved, which directly leads to greater clinical effectiveness.

Another embodiment of the invention is pharmaceutical product comprising an orally administerable solid dosage form comprising a matrix formed of at least one pharmaceutically acceptable material, an effective amount of an allergen for desensitizing a human to said allergen, said dosage form having an allergen content at least about 50% of the initial allergen content after being held for 3 months at 25° C. and 60% relative humidity. Preferably said pharmaceutical product is in form of a lozenge, tablet, a capsule or a caplet.

The fast-dispersing solid dosage form according to the invention can be prepared by a sublimation process according to the process disclosed in U.S. Pat. No. 4,371,516. Accordingly, a solidified solution of the allergen and the matrix forming excipients is subjected to sublimation. The sublimation process is preferably carried out by freeze-drying the solution. The solution is contained in a depression of the multi dosage container during the freeze-drying step to produce a solid form in any desired shape. The multi dosage container can be cooled using liquid nitrogen or solid carbon dioxide. After the freezing step the frozen solution in the multi dosage container is subjected to reduced pressure and, if desired, controlled application of heat to aid the sublimation of the solvent.

The invention further includes the use of an allergen for the manufacture of a stable, fast-dispersing, non-compressed allergen vaccine solid dosage form with low friability comprising (a) a matrix, and (b) at least one allergen form for use in the treatment of allergy or alleviating symptoms of allergy.

In another embodiment a method is provided of producing a fast-dispersing, non-compressed solid and stable dosage form suitable for oromucosal administration having low friability comprising at least one matrix forming agent and an effective dose for desensitizing an individual to at least one allergen, comprising the steps of
(a) preparing an aqueous solution comprising said at least one allergen and at least one matrix forming agent,
(b) introducing the solution into one or more depressions in a mould
(c) subjecting the loaded sheet to freezing and freeze-drying using standard conditions of shelf temperature and chamber pressure to obtain said solid dosage form in each depression.

In yet another embodiments a method is provided of producing a fast-dispersing, non-compressed solid and stable dosage form suitable for oromucosal administration having low friability comprising at least one matrix forming agent and an effective dose for desensitizing an individual to at least one allergen, comprising the steps of
(a) preparing an aqueous solution comprising said at least one allergen and at least one matrix forming agent,
(b) introducing the solution into depressions in a laminated blister sheet
(c) subjecting the loaded sheet to freezing and freeze-drying using standard conditions of shelf temperature and chamber pressure to obtain said solid dosage form in each depression.

In a preferred embodiment of the method the blister sheet is an all aluminium blister sheet. In a particularly preferred embodiment of the method, the blister sheet is a multilayered, all aluminium blister sheet.

In yet another embodiment a method is provided for obtaining a pharmaceutical product comprising a fast-dispersing, non-compressed solid and stable dosage form suitable for oromucosal administration comprising at least one matrix forming agent and an effective dose for desensitizing an individual to at least one allergen, said dosage form having low friability comprising
1) producing a stable fast-dispersing, non-compressed solid dosage form,
2) measuring the friability of said dosage form in an assay comprising the steps of,
(a) placing individual sealed blisters each containing a solid dosage form in equipment suitable for friability measurements;
(b) moving the sealed blister containing the solid dosage form for an appropriate time and at an appropriate velocity;
(c) removing the sealed blister containing the solid dosage form;
(d) opening the blister and placing the solid dosage form and any residues in a container;
(e) removing the solid dosage form unit from the container leaving any loose residuals in said container;
(f) performing an allergen specific assay on said residues determining the major allergen content of at least one major allergen in said residues; and
(g) calculating the percentage of at least said major allergen in said residues of the total major allergen content of the solid dosage form unit.
detecting whether the dosage form fulfils the requirements for low friability, and
3) repeating 1) and 2) until the requirements for the dosage form is fulfilled.

Oromucosal immunotherapy can be regarded as a way of inducing tolerance and inducing mucosal vaccination. The mucosa of the mouth is rich in dendritic cells with a strong potential for antigen presentation. The dendritic cells are believed to process the allergens and then migrate to the local lymph nodes where they present allergen derived peptides to allergen specific T cells. During sublingual immunotherapy this dendritic cell—T cell interaction is believed to induce T cells with regulatory potential or to increase the ratio of allergen specific Th1 cells to allergen specific Th2 cells. A number of immunological parameters monitored during the allergy vaccination may be suitable markers for effects or efficacy of the treatment, alone or in combination respectively. These include systemic and mucosal antibody responses e.g. specific IgA, IgG and IgE antibodies; cytokine levels e.g. INFgamma, IL-2, IL-4, IL-5, IL-10, IL-12 and TNF alpha in blood or mucosal secretions; activation, chemotaxis, proliferation, signaling, cytokine production and other responses of regulatory T-cells, Th1 cells, TH2 cells, CD8 cells, other T cell subsets or B-cells or NK cells, and cell surface marker expression such as CD (cluster of differentiation) markers e.g. CD4, CD8, CD23, CD25, CD62L, CLA, beta7, CCR9, CD69, CD45RO, CCR3, CXCR5, effector cell function such as total histamine content of basophils; eosinophil, basophil, lymphocyte, monocyte numbers in blood, tissue and secretions; eosinophil, basophil, lymphocyte, monocyte mediator release, cytokine production, activation, chemotaxis, proliferation, signalling and other responses.

In a preferred embodiment a vaccine according to the present invention has a profile where one or more of the following immunological changes can be found; an increased allergen specific IgG response, an increased allergen specific IgA response, reduced allergen specific IgE response, few local side effects; reduced allergen specific effector responses of eosinophils, basophils, lymphocytes and/or monocytes; induction of T cells with regulatory potential, increased ratio of allergen specific Th1 cells to allergen specific Th2 cells, induction of other cells with regulatory potential, reduced allergen specific Th2 response.

Allergy is also a known disease in animals especially domestic and companion ship animal. It is known in the art that they develop allergies toward numerous allergen sources including grass, house dust mites, and parasites.

Hematophagous, i.e. bloodsucking insect infestation is known to lead to a hypersensitive response called flea allergic dermatitis (FAD). In a preferred embodiment of the current invention allergens for animal vaccines include allergens originating or transferred from parasites like ectoparasites (e.g. fleas, ticks, mosquitoes, flies), parasitic helminth venom (like heart worm e.g. *Dirofilaria* or onchocerciasis e.g. *Onchocerca*) and house dust mite. More preferred are saliva allergens from fleas like *Ctenocephalides* e.g. *C. canis* and *C. felis*, hard ticks likes *Ixodes*, Arnblyomma, soft ticks like Ornithodoros and from midges like *Culicoides*.

Water Content:

The residual water was determined using a Karl Fischer titration principle. The method gives a quantitative determination of the water content in a sample based on the principle that a given amount of $I_2$ leads to transformation of an equivalent amount of $H_2O$.

In short, 1-3 solid dosage form per vial were tested in triplicates in a Karl Fisher Titrator according to the manufactures instruction together with blind samples (4 per run) and KF standard samples see Example 10.

Total Allergenic Activity:

The test was performed using LIA (described in Eiken et al., Allergy 1992, 47:495-497), which is a competitive immunoassay. 100 μl anti human IgE monoclonal antibody bound to paramagnetic particles (PMP) (ADVIA Centaur PMP, ALK-Abelló A/S, Denmark) were washed×3 and 100 μl of a pool of patient sera with specific *Phleum pratense* IgE antibodies were added and were incubated on a shaker for 2 hours at 2-8° C., whereby specific IgE binds to the PMP. The PMP were washed to remove IgG antibodies×3 with gelatine buffer. Ten solid dosage forms were dissolved in gelatine buffer and dilutions were prepared of 625 SQ-Units or 1250 SQ-Units per tablet. Samples or references of a known content of biotinylated *Phleum pratense* API were applied and incubated overnight on a shaking at 2-8° C. The samples and the biotinylated API will compete for the IgE binding sites, when the concentration of allergen in the sample rise, the amount of bound biotinylated API will drop. After incubation the samples were washed×3 in gelatine buffer, and LITE-reagent for example, streptavidin coupled acridinium ester chemiluminescent compound (ADVIA Centaur Lite Reagens, ALK-Abelló A/S is applied. The samples were incubated for 2 hours on a shaker at 2-8° C., washed in gelatine buffer×3 and read in a luminometer. The response is inversely related to the concentration of the allergen in the sample.

Major Allergen Content:

The test was performed using ELISA technique according to Obispo et al, Allergy, 1997, 52, pg. 806-813.

The ELISA method measures the concentration of *Phleum pratense* major allergen 5(Phl p 5). Two monoclonal antibodies (ALK-Abelló A/S, DK) reacting with different epitopes on the Phl p 5 molecule were coated to the microtiterplate the night over at 4° C. After washing (4 times with washing buffer, 0.1 M PBS, 0.05% Tween-20) and blocking the plate with blocking buffer (2% Caseinbuffer), samples/references, which then binds to the antibodies, were applied. After washing again (4 times with washing buffer) biotinylated rabbit polyclonal antibodies (ALK-Abelló A/S, DK) against *Phleum pratense* antigens were applied to the wells and allowed to react.

After 4 times washing with wash buffer, streptavidin coupled to HRP (horse radish peroxidase) (DAKO, Denmark) was applied to the wells and allowed to react for 1 hour at room temperature (shaking). After washing 4 times with washing buffer substrate (TMB, KEM EN TEC) for the HRP enzyme was applied and allowed to react for 20 min, the reaction was then stopped with 0.5 N sulphuric acid. The colour developed was measured at 450 nm in a spectrophotometer e.g. Multilabel counter Victor 2.

Friability:

The friability of the fast-dispersing dosage forms was measured using the following method.

A sealed blister sheet containing 10 blisters, each of the blisters containing a solid dosage form, was cut apart into 10 individual blisters and each blister was placed in a piece of equipment suitable for friability measurements as described in EP $3^{rd}$ ed. V. 2.9.7 and the units were rotated 100 turns at 25±1 rpm. The individual blisters were removed, opened and the solid dosage form was transferred to a suitable container. The solid dosage form was then removed from the container, leaving any loose residues in said container. An immunochemical allergen specific assay (ELISA) was carried out to detect the amount of allergen content in the residues (see above).

Stability Results:

TABLE 2

Product Dosage form containing *Phleum pratense* 2500 SQ-U

| Sampling (month) | Friability % loss of total content of extract (API) | Disintegration (sec.) | Water content (%) | Visual inspection | Major allergen content (%) | Total allergenic activity (%) |
|---|---|---|---|---|---|---|
| Storage condition: 25° C./60% RH | | | | | | |
| Start | 0.000 | 8 | 5.5 | Comply | 96 | 101 |
| 1 | n.m. | 5 | 4.9 | Comply | 79 | 91 |
| 2 | n.m. | 6 | 5.4 | Comply | 96 | 102 |
| 3 | 0.000 | 5 | 5.2 | Comply | 94 | 82 |
| 6 | n.m. | n.m. | n.m. | n.m. | n.m. | n.m. |
| 9 | 0.000 | 5 | 5.3 | Comply | 83 | 105 |
| Storage condition: 40° C./75% RH | | | | | | |
| 1 | n.m. | 3 | 4.8 | Comply | 85 | 86 |
| 2 | n.m. | 8 | 5.2 | Comply | 85 | 100 |
| 3 | 0.005 | 6 | 5.4 | Comply | 94 | 83 |
| 6 | n.m. | n.m. | n.m. | n.m. | n.m. | n.m. |
| 9 | 0.005 | 4 | 5.1 | Comply | 70 | 92 |

TABLE 3

Product Dosage form containing *Phleum pratense* 25000 SQ-U

| Sampling (month) | Friability % loss of total content of extract (API) | Disintegration (sec.) | ID | Water content (%) | Visual inspection | Major allergen content (%) | Total allergenic activity (%) |
|---|---|---|---|---|---|---|---|
| Storage condition: 25° C./60% RH | | | | | | | |
| Start | 0.000 | 8 | Comply | 6.3 | Comply | 106 | 104 |
| 1 | n.m. | n.m. | Comply | n.m. | n.m. | n.m. | n.m. |
| 2 | n.m. | n.m. | Comply | n.m. | n.m. | n.m. | n.m. |
| 3 | n.m. | n.m. | Comply | n.m. | n.m. | n.m. | n.m. |
| 6 | n.m. | 7 | Comply | n.m. | Comply | 87 | 141 |
| 9 | 0.000 | 4 | Comply | 5.1 | Comply | 79 | 105 |
| Storage condition: 40° C./75% RH | | | | | | | |
| 1 | n.m. | n.m. | Comply | n.m. | n.m. | n.m. | n.m. |
| 2 | n.m. | n.m. | Comply | n.m. | n.m. | n.m. | n.m. |
| 3 | 0.005 | n.m. | Comply | n.m. | n.m. | n.m. | n.m. |
| 6 | n.m. | 6 | Comply | n.m. | Comply | 84 | 135 |
| 9 | 0.005 | 4 | Comply | 5.0 | Comply | 77 | 105 |

TABLE 4

Product Dosage form containing *Phleum pratense* 125000 SQ-U

| Sampling (months): | Friability % loss of total content of extract (API) | Disintegration (sec.) | ID | Water content (%) | Visual inspection | Major allergen content (%) | Total allergenic activity (%) |
|---|---|---|---|---|---|---|---|
| Storage condition: 25° C./60% RH | | | | | | | |
| Start | 0.000 | 5 | Comply | 4.7 | Comply | 100 | 100 |
| 1 | n.m | 10 | Comply | 3.9 | Comply | 84 | 93 |
| 2 | n.m. | 5 | Comply | 4.5 | Comply | 92 | 104 |
| 3 | n.m. | 8 | Comply | 4.8 | Comply | 80 | 88 |
| 6 | n.m. | 6 | Comply | n.m. | Comply | n.m. | n.m. |
| 9 | 0.003 | 5 | Comply | 4.5 | Comply | 77 | 106 |
| Storage condition: 40° C./75% RH | | | | | | | |
| 1 | n.m. | 4 | Comply | 4.1 | Comply | 90 | 92 |
| 2 | n.m. | 6 | Comply | 4.6 | Comply | 91 | 109 |
| 3 | 0.001 | 7 | Comply | 4.5 | Comply | 83 | 89 |
| 6 | n.m. | 5 | Comply | n.m. | Comply | n.m. | n.m. |
| 9 | n.m. | 5* | Comply | 4.6 | Comply | 78 | 118 |

*Mean value of only 3 dosage forms

Example 2. Allergen Vaccine Containing *Phleum pratense* Grass Pollen Extract and Starch Composition

TABLE 5

| Ingredients | Unit | Dosage form 1 | Dosage form 2 | Dosage form 3 | Function |
|---|---|---|---|---|---|
| Drug substance: | | | | | |
| *Phleum pratense* | SQ-U | 2500 | 25000 | 125000 | API |
| | mg extract | 0.0047 | 0.047 | 0.235 | |

TABLE 5-continued

| Ingredients | Unit | Dosage form 1 | Dosage form 2 | Dosage form 3 | Function |
|---|---|---|---|---|---|
| Other ingredients | | | | | |
| Purified water | Mg | q.s to 250 mg | q.s to 250 mg | q.s to 250 mg | solvent |
| Pre-gelatinised starch | Mg | 8 mg | 9 mg | 11 mg | Matrix |
| Mannitol | Mg | 8 mg | 9 mg | 11 mg | Matrix |
| Sodium hydroxide | Mg | q.s | q.s | q.s | pH adjustment to 7.5 |

Manufacturing Process:

Same as example 1, pre-gelatinised starch was added instead of gelatine (fish source). The solid dosage form had an average weight of 19 mg and average diameter of 11 mm.

Short Descriptions of Analytical Methods:

Same as example 1.

Stability Results:

TABLE 6

Product Dosage form containing *Phleum pratense* 2500 SQ-U

| Sampling (months): | Friability % loss of total content of extract (API) | Disinte-Gration (sec.) | Water content (%) | Visual inspection | Total allergenic activity (%) |
|---|---|---|---|---|---|
| Storage condition: 25° C./60% RH | | | | | |
| Start | 0.008 | 8 | 3.5 | Comply | 101 |
| 1 | n.m. | 5 | 3.0 | Comply | 80 |
| 2 | n.m. | 6 | 3.6 | Comply | 99 |
| 3 | 0.021 | 5 | 3.9 | Comply | 69 |
| 6 | n.m. | n.m. | n.m. | n.m. | n.m. |
| 9 | 0.010 | 5 | 3.5 | Residues | 101 |
| Storage condition: 40° C./75% RH | | | | | |
| 1 | n.m. | 3 | 2.9 | Comply | 74 |
| 2 | n.m. | 8 | 3.7 | Comply | 98 |
| 3 | 0.022 | 6 | 4.3 | Comply | 73 |
| 6 | n.m. | n.m. | n.m. | n.m. | n.m. |
| 9 | 0.003 | 4 | n.m. | Residues | 75 |

TABLE 7

Product Dosage forms containing *Phleum pratense* 25000 SQ-U

| Sampling (months): | Friability % loss of total content of extract (API) | Disintegration (sec.) | ID | Water content (%) | Visual inspection | Total allergenic activity (%) |
|---|---|---|---|---|---|---|
| Storage condition: 25° C./60% RH | | | | | | |
| Start | 0.022 | 10 | Comply | 3.3 | Comply | 106 |
| 1 | n.m. | n.m. | Comply | n.m. | n.m. | n.m. |
| 2 | n.m. | n.m. | Comply | n.m. | n.m. | n.m. |
| 3 | n.m. | n.m. | Comply | n.m. | n.m. | n.m. |
| 6 | n.m. | n.m. | n.m. | n.m. | n.m. | n.m. |
| 9 | 0.010 | 160 | n.m. | 3.5 | Residues | 99 |
| Storage condition: 40° C./75% RH | | | | | | |
| 1 | n.m. | n.m. | Comply | n.m. | n.m. | n.m. |
| 2 | n.m. | n.m. | Comply | n.m. | n.m. | n.m. |
| 3 | n.m. | n.m. | Comply | n.m. | n.m. | n.m. |
| 6 | n.m. | n.m. | n.m. | n.m. | n.m. | n.m. |
| 9 | 0.050 | 60 | n.m. | 3.4 | Residues | 96 |

TABLE 8

Product Dosage forms containing *Phleum pratense* 125000 SQ-U

| Sampling (months): | Friability % loss of total content of extract (API) | Disintegration (sec.) | ID | Water content (%) | Visual inspection | Total allergenic activity (%) |
|---|---|---|---|---|---|---|
| Storage condition: 25° C./60% RH | | | | | | |
| Start | 0.041 | 11 | Comply | 2.6 | Comply | 121 |
| 1 | n.m | 18 | Comply | 2.4 | Residues | 102 |
| 2 | n.m. | 30 | Comply | 3.0 | Residues | 126 |
| 3 | 0.055 | 28 | Comply | 3.6 | Residues | 102 |
| 6 | n.m. | n.m. | n.m. | n.m. | n.m. | n.m. |
| 9 | 0.0030 | 58 | n.m. | 2.9 | Residues | 99 |
| Storage condition: 40° C./75% RH | | | | | | |
| 1 | n.m. | 58 | Comply | 2.5 | Residues | 96 |
| 2 | n.m. | 25 | Comply | 3.1 | Residues | 121 |
| 3 | 0.033 | 25 | Comply | 3.5 | Residues | 97 |
| 6 | n.m. | n.m. | n.m. | n.m. | n.m. | n.m. |
| 9 | n.m. | 70 | n.m. | 2.7 | Residues | 110 |

Example 3. Allergen Vaccine Containing Grass Extract and Fish Gelatin

TABLE 9

| Ingredients | Unit | Dosage form 1 | Dosage form 2 | Dosage form 3 | Function |
|---|---|---|---|---|---|
| Active substance: | | | | | |
| *Phleum pratense* | SQ-U | 2500 | 25000 | 75000 | Active substance |
| | mg extract | 0.0047 | 0.047 | 0.141 | |
| Other ingredients | | | | | |
| Purified water | mg | q.s. to 250 mg | q.s. to 250 mg | q.s. to 250 mg | Solvent |
| Gelatine (fish source)* | mg | 16 | 16 | 16 | Matrix |
| Mannitol | mg | 14 | 14 | 14 | Matrix |
| Sodium hydroxide | mg | q.s. | q.s. | q.s. | pH adjustment 7.5 |

Manufacturing Process:
Same as example 1
The solid dosage form had an average weight of 30 mg and average diameter of 12 mm.

Short Descriptions of Analytical Methods:
Same as example 1, except friability and stability were not measured.

Results of Analysis:

TABLE 10

| | Test Methods | | | |
|---|---|---|---|---|
| Strengths | Major allergen content (%) ELISA | Total allergenic activity (%) LIA | Disintegration (sec.) | Water content (%) |
| 2500 SQ-U/dosage form | 97 | 102 | 1 | 5.5 |
| 25000 SQ-U/dosage form | 100 | 89 | 1 | 5.3 |
| 75000 SQ-U/dosage form | 94 | 95 | 1 | 5.2 |

The results provide an embodiment of an allergen containing solid dosage form comprising three different doses of grass allergen extract in a matrix forming agent consisting of 6.5% fish gelatin and 5.5% mannitol. The allergen content and allergenic activity in the dosage forms were within the acceptable limits (see below) following manufacture. Further, the results shows that all dosage forms have a water content in the preferred range of 4-7%.

Results

As apparent from Examples 1, 2, and 3 it is possible to manufacture fast-dispersing solid allergen vaccine dosage forms which disintegrate instantaneously. The loss of total content of extract was found to be acceptable, even though the visual inspection resulted in the detection of residues in some of the blister packs (predominantly to a higher degree for starch containing matrixes), the amount of the residue i.e. allergen content loss is within the acceptable limit, i.e less than 0.5 μg extract. Thus, it is possible to manufacture non-compressed fast-dispersing solid dosage forms with low friability containing allergens.

The stability data show that the formulations are stable at room temperature and at elevated temperature and humidity for nine months. The allergen content and total allergen activity remained unchanged (within assay variation and according to EP 3rd ed. monograph for Allergen Products; total allergen activity 50-200% of theoretical value, major allergen content 65-135% of theoretical value).

All manufactured batches were subjected to visual inspection and found within the acceptable limit.

Example 4: Allergen Vaccine Compositions

Solid allergen vaccine dosage forms were prepared containing varying ratios of matrix forming agents.

TABLE 11

Solid dosage form containing 75,000 SQ-U *Phleum pratense* grass pollen extract prepared in different packs

| % gelatin | % mannitol | Pack type | Load to Fracture (Kgf) | Disintegration times (sec.) |
|---|---|---|---|---|
| 4.00 | 3.00 | 5 layer foil | 0.158 | <2 |
| 4.00 | 3.00 | PVC/PVdC | 0.199 | <2 |
| 5.00 | 3.75 | 5 layer foil | 0.296 | <2 |
| 5.00 | 3.75 | PVC/PVdC | 0.264 | <2 |
| 6.00 | 4.50 | 5 layer foil | 0.342 | <2 |
| 6.00 | 4.50 | PVC/PVdC | 0.386 | <2 |
| 7.00 | 5.25 | 5 layer foil | 0.491 | <2 |
| 7.00 | 5.25 | PVC/PVdC | 0.421 | <2 |

All dosage forms were prepared in blister pack having a unit diameter of 12 mm as described previously. All dosage forms disintegrated rapidly and were robust as assessed by visual appearance, tensile strength and peak load to facture.

TABLE 12

Solid dosage forms containing 75000 SQ-Units of *Phleum pratense* grass pollen extract in fish gelatine and mannitol.

| % gelatin | % mannitol | Tensile strength ($N/mm^{-2}$) | Peak load to Fracture (Kgf) | Disintegration times (sec. |
|---|---|---|---|---|
| 5 | 4 | 0.239 | 0.168 | <2 |
| 6.5 | 5 | 0.361 | 0.265 | <2 |
| 6.5 | 5.5 | 0.425 | 0.277 | <2 |
| 5 | 7 | 0.389 | 0.239 | <2 |
| 8 | 4 | 0.531 | 0.308 | <2 |
| 8 | 7 | 0.708 | 0.465 | <2 |
| 7 | 7 | 0.543 | 0.355 | <2 |
| 7 | 5 | 0.458 | 0.311 | <2 |
| 6 | 4 | 0.263 | 0.169 | <2 |
| 6 | 7 | 0.381 | 0.265 | <2 |

All dosage forms were prepared in blister pack having a unit diameter of 12 mm as described previously.

All dosage forms disintegrated rapidly and were robust as assessed by visual appearance and Peak load to fracture.

Example 5 Uniformity

Dosage forms according to composition and manufacture as described in example 1 where tested for uniformity of allergen content. The allergen content was determined as uniformity of potency of grass pollen *Phleum* p 5 by an ELISA assay as described in example 1 for the dosage form containing 25000 and 125000 SQ-Units respectively. 10 individual units from a blister pack were compared as shown in table 13 and 14.

TABLE 13

Uniformity of content of 25000 SQ-Unit dosage form.

| ID (dosage form no.) | % of total allergen content |
|---|---|
| 1 | 97.0 |
| 2 | 98.6 |
| 3 | 97.7 |
| 4 | 95.6 |
| 5 | 97.2 |
| 6 | 99.3 |
| 7 | 95.7 |
| 8 | 96.9 |
| 9 | 97.4 |
| 10 | 98.3 |
| mean value | 97.4 |

TABLE 14

Uniformity of content of 125,000 SQ-Unit dosage form

| ID (dosage form no.) | % of total allergen content |
|---|---|
| 1 | 101.4 |
| 2 | 102.4 |
| 3 | 102.3 |
| 4 | 101.9 |
| 5 | 104.4 |
| 6 | 100.5 |
| 7 | 101.1 |
| 8 | 104.0 |
| 9 | 113.4 |
| 10 | 97.1 |
| mean value | 102.8 |

All variations were within acceptable limits and good uniformity of allergen content was found.

Example 6. Administration of a *Phleum pratense* Grass Pollen Vaccine to Dogs

Dogs were equally distributed in respect to sex within each study group and were dosed following according to table 15

TABLE 15

Group assignment

| Group | dose level (in SQ-units) | Number of dosage forms[a] | Number of dogs | Number of recovery dog |
|---|---|---|---|---|
| 1 | 0 | 1 | 8 | 4 |
| 2 | 25000 | 1 | 8 | — |
| 3 | 500000 | 4 | 8 | 4 |

[a]Group 1 received placebo dosage forms, group 2 received 25000 and group 3 received 125000 SQ-Unit dosage forms prepared according to example 1

The dogs were administered doses as indicated in Table 15 sublingually. The dosage form was placed under the tongue and the snout was held closed to allow dissolution of the dosage form. The animals were dosed once per day for a period of 4 consecutive weeks. Blood samples were drawn for all dogs in every group after the completion of the treatment period. 4 dogs in the placebo and the high dose group respectively continued through a recovery period of 4 weeks where after further blood sample were drawn.
Method:
*Phleum pratense* (Phl p) specific IgG in either serum or plasma was determined as follows: ELISA plates (Costar) were coated with 10 µg/ml Phl p extract over night at 4° C. The plates were washed 4 times with 1 min soak in between and blocked against unspecific binding with 2% Casein buffer for one hour at room temperature. Individual serum or plasma samples were diluted in polypropylene plates, transferred to the ELISA plates and incubated for two hours at room temperature. After washing, HRP marked anti-dog IgG (ICN) was added to the ELISA plates and incubated for one hour at room temperature. After another wash, TMB was added to the ELISA plates, covered and incubated for 20 min at room temperature. The reaction was stopped with 0.5M sulphuric acid. The absorbance (OD) was measured in a spectrophotometer at 450 nm.

The OD values at 1:200 dilution were compared for the dogs in the three groups: placebo, 25000 SQ/dose and 500000 SQ/dose. Statistical difference between the three groups was calculated with the Mann-Whitney rank sum test which is a nonparametric test that compares two unpaired groups. Dogs receiving 500000 SQ units had higher mean value than both 25000 and placebo indicating a specific antibody response.
Results:

P values from the Mann-Whitney test are depicted in Table 16.

TABLE 16

| Groups | P value |
|---|---|
| Placebo vs 25000 SQ-U/dose | 0.059 |
| Placebo vs 500000 SQ-U/dose | 0.004 |

P-level ≤ 0.05 = significant with a 95% certainty.

There is a clear significant difference between the placebo and the 500,000 SQ-U/dose group indicating that sublingual treatment with 500,000 SQ-U/dose for 4 weeks gives a higher humoral specific IgG level. There is a borderline significant difference between the placebo and 25,000 SQ-U/dose group also indicating that treatment with 25,000 SQ-U/dose gives a humoral specific IgG level, although weaker than treatment with 500000 SQ-U/dose.

Example 7. Administration of a *Phleum pratense* Grass Pollen Vaccine to Allergics Allergic patients, both female and male aged 18-65 years, with a diagnosis of grass pollen allergy were administered sublingual doses as one, two or three single doses and/or as multiple doses of a grass pollen extract containing solid dosage form, according example 1, in a randomised, double-blind, placebo-controlled designed trial.

Safety/tolerability was assessed with progressing single doses. Single doses of placebo, 2,500, 25,000, 75,000, 125,000 and 375,000 SQ-U were administered stepwise in a dose-escalating fashion using combinations of placebo and active tablets (12 mm in diameter and approximately 18 mg dry weight) to give the required dose. Forty-seven patients with allergy to grass pollen were treated. The dosage forms were placed under the tongue and held there for 1 minute before swallowing. Eating and drinking was prohibited for 5 minutes after application of the solid dosage form. The patients were observed for 2 hours for symptoms. All side effects were recorded, and after each dose the patients recorded tolerability on a Visual Analogous Scale. The dosage form containing the doses were found to be well tolerated up to and including 125,000 SQ-U as adverse events were predominantly mild in severity and limited to 'itching' phenomena in the mouth and throat. Adverse events were also reported in the placebo group. 'Itching mouth' was reported more frequently with increased dose for example, a progression of adverse events correlated with progressing doses.

Further, safety/tolerability of repeated doses was tested for three selected doses, 2,500, 25,000 and 75,000 SQ-U, and placebo. Forty-seven patients with allergy to grass pollen, distributed in four groups of comparable size, received a daily sublingual dosage for a period of 8 weeks. Combinations of three tablets containing placebo, 2,500 and/or 25,000 SQ-U (12 mm in diameter and approximately 18 mg dry weight) were applied to obtain the required doses. Adverse events were recorded and symptoms were collected in patient diaries. The doses contained in the dosage form were found to be well tolerated in all three active treatment groups. Adverse events and symptoms were reported more frequently with increased dose.

Thus, the solid dosage forms tested are feasible for clinical use in both escalating dose and singular repeated dose therapy Example 8. Allergen Vaccine Containing *Phleum pratense* Grass Pollen Extract and Fish Gelatine Solid dosage forms as described according to example 1 table 1 and manufactured according to example 1 were stored for 12 month at 25° C./60% RH and evaluated by measurement of visual inspection, disintegration, water content, uniformity of mass, identity (protein profile), major allergen content and total allergenic activity. All test were performed as described in example one. An average of a determination made in duplicate on a pool of 10 tablets is shown unless otherwise stated.

TABLE 17

Storage conditions: 25° C./60% RH

Product: 2500 SQ-U/tablets

Test:

| | Visual inspection | Uniformity of mass | Disintegration (seconds) | Total allergenic activity. (LIA) | Major allergen content. (ELISA) | Friability | Water content (%) |
|---|---|---|---|---|---|---|---|
| 0 | Comply | Comply | 6 | 122% | 97% | 0.00% | 6.1% |
| 12 | Comply | Comply | 1 | 105% | 99% | N/A | 4.8% |

TABLE 17-continued

Storage conditions: 25° C./60% RH

Test:

| | Visual inspection | ID (SDS-page) | Uniformity of mass | Disintegration (seconds) | Total allergenic activity. (LIA) | Major allergen content. (ELISA) | Friability | Water content (%) |
|---|---|---|---|---|---|---|---|---|
| | | | | Product 25000 SQ-U/tablets | | | | |
| 0 | Comply | Comply | Comply | 5 | 108% | 100% | 0.00% | 5.7% |
| 12 | N/A | Comply | N/A | N/A | N/A | N/A | N/A | N/A |
| | | | | Product 125000 SQ-U/tablets | | | | |
| 0 | comply | Comply | Comply | 7 | 110% | 99% | 0.00% | 5.4% |
| 12 | comply | Comply | Comply | 1 | 119% | 104% | N/A | 4.2% |

Visual Inspection:
There were no changes in the appearance of the tablets during the study.

Disintegration:
There were no remarkable changes in the disintegration time during the study. All test samples disintegrated immediately.

Uniformity of Mass:
There were no remarkable changes in the uniformity of mass during the study (assessment of 20 tablets).

Water Content:
There were no remarkable changes in the water content during the study.

Identity SDS-Page:
There were no dramatic changes in the protein profile during the study; the samples were similar to the reference at all test times.

Total Allergenic Activity:
No significant loss of total allergen activity was measured for the tablets (varies from 105%-119% of the theoretical content for the different strengths at 12 month, values which are within the deviation of the test performed).

Major Allergen Content:
No significant loss of allergen content as determined by major allergen content was measured for the tablets (varies from 99%-104% of the theoretical content for the different strengths at 12 month storage, values which are within the deviation of the test performed).

Example 9. Allergen Vaccine Containing *Phleum pratense* Grass Pollen Extract and Fish Gelatine The composition is as described in example 1, table 1

Solid dosage forms manufactured according to example 1 were stored for 18 month at 25° C./60% RH and evaluated by visual inspection of the dosage form, i.e. tablets, and by determining the disintegration time, water content, uniformity of mass, identity (protein profile), major allergen content and total allergenic activity. All tests were performed as described in example 1. An average of a determination made in duplicate on a pool of 10 tablets is shown unless otherwise stated.

TABLE 18

Storage conditions: 25° C./60% RH

Product 2500 SQ-U/tablets

Test:

| | Visual inspection | Uniformity of mass | Disintegration (seconds) | Total allergenic activity. (LIA) | Major allergen content. (ELISA) | Friability | Water content (%) |
|---|---|---|---|---|---|---|---|
| 0 mth | Comply | Comply | 6 | 122% | 97% | 0.00% | 6.1% |
| 18 mth | Comply | Comply | 1 | 115% | 90% | N/A | 5.0 |

Product 125000 SQ-U/tablets

Test:

| | Visual inspection | ID (SDS-page) | Uniformity of mass | Disintegration (seconds) | Total allergenic activity. (LIA) | Major allergen content. (ELISA) | Friability | Water content (%) |
|---|---|---|---|---|---|---|---|---|
| 0 mth | Comply | Comply | Comply | 7 | 110% | 99% | 0.00% | 5.4% |
| 18 mth | Comply | Comply | Comply | 1 | 117% | 94% | N/A | 4.4% |

Mth = month(s)
N/A = not analysed

For solid dosage form containing 25,000 SQ-Unit/solid dosage form only analyses of ID were performed. Similar ID pattern was found after 18 months of storage as compared to 0 month (data not shown).

The solid dosage form were found to be stable, i.e. allergen content and total allergen activity remained unchanged (within assay variation and according to EP $3^{rd}$ ed. monograph for Allergen Products; total allergen activity 50-200% of theoretical value major allergen content 65-135% of theoretical value), after storage for 18 months at 25° C./60% RH. Further, there were no changes in the appearance of the solid dosage forms for all the tested allergen doses during the study. Further, there were no changes in the uniformity of mass of the dosage forms tested during the study. As to the water content, no noticeable changes were and within the preferred range of 4-7%.

Example 10. Allergen Vaccine Containing *Phleum pratense* Grass Pollen Extract and Fish Gelatin The composition of the solid dosage forms is shown in table 9 of example 1.

The solid dosage forms were prepared according to example 1 and submitted to stability testing.

All tests were performed according to example 1.

Stability Results

TABLE 19

Product 2500 SQ-U/dosage form

| Sampling (months): | Visual inspection | Disintegration | Total allergenic activity. (LIA) | Major allergen content. (ELISA) | Water content (%) |
|---|---|---|---|---|---|
| Storage conditions: 25° C./60% RH ||||||
| 0 | Comply | 1 sec. | 129% | 82% | 5.0% |
| 1 | Comply | 1 sec | 87% | 98% | 5.3% |
| 3 | Comply | 1 sec | 130% | 116% | 5.2% |
| 6 | Comply | 1 sec | 97% | 100% | 5.2% |
| Storage condition: 40° C./75% RH ||||||
| 1 | Comply | 1 sec | 97% | 90% | 5.2% |
| 3 | Comply | 1 sec. | 124% | 114% | 5.5% |
| 6 | Comply | 1 sec | 101% | 93% | 5.9% |

TABLE 20

Product 25000 SQ-U/dosage form

| Sampling (months): | Visual inspection | ID (SDS-page) | Disintegration | Total allergenic activity. (LIA) | Major allergen content. (ELISA) | Water content (%) |
|---|---|---|---|---|---|---|
| Storage conditions: 25° C./60% RH |||||||
| 0 | Comply | Similar to reference | 1 sec. | 101% | 93% | 4.7% |
| 1 | n.m | Similar to reference | n.m | n.m. | n.m | n.m |
| 3 | n.m | Similar to reference | n.m | n.m | n.m | n.m |
| 6 | n.m | Similar to reference | n.m | n.m | n.m | n.m |
| Storage condition: 40° C./75% RH |||||||
| 1 | Comply | Similar to reference | n.m | n.m | n.m | n.m |
| 3 | Comply | Similar to reference | n.m | n.m | n.m | n.m |
| 6 | Comply | Similar to reference | n.m | n.m | n.m | n.m | n.m. = not measured

TABLE 21

Product 75000 SQ-U/dosage form

| Sampling (months): | Visual inspection | ID (SDS-page) | Disintegration | Total allergenic activity. (LIA) | Major allergen content. (ELISA) | Water content (%) |
|---|---|---|---|---|---|---|
| Storage conditions: 25° C./60% RH |||||||
| 0 | Comply | Similar to reference | 1 sec. | 109% | 77% | 5.3% |
| 1 | Comply | Similar to reference | 1 sec | 75% | 92% | 5.1% |
| 3 | Comply | Similar to reference | 1 sec | 113% | 108% | 5.0% |

TABLE 21-continued

Product 75000 SQ-U/dosage form

Test:

| Sampling (months): | Visual inspection | ID (SDS-page) | Disintegration | Total allergenic activity. (LIA) | Major allergen content. (ELISA) | Water content (%) |
|---|---|---|---|---|---|---|
| 6 | Comply | Similar to reference | 1 sec | 99% | 95% | 5.2% |
| Storage condition: 40° C./75% RH | | | | | | |
| 1 | Comply | Similar to reference | 1 sec | 79% | 92% | 5.3% |
| 3 | Comply | Similar to reference | 1 sec. | 105% | 100% | 5.5% |
| 6 | Comply | Similar to reference | 1 sec | 99% | 95% | 5.9% |

The quality of the dosage forms were judged by visual inspection of the dosage form (i.e. tablets) and by determining the disintegration time, water content, uniformity of mass, identity (protein profile), major allergen content and total allergenic activity (not all data are shown).

The solid dosage form in all doses were found to be stable, i.e. allergen content and total allergen activity remained unchanged (within assay variation and according to EMEA $3^{rd}$ ed. monograph for Allergen Products; total allergen activity 50-200% of theoretical value, major allergen content 65-135% of theoretical value), after storage for 6 months at 25° C./60% RH and 40° C./75% RH. Further, there were no changes in the appearance of the solid dosage forms for all the tested allergen doses during the study. Further, there were no changes in the uniformity of mass of the dosage forms tested during the study. As to the water content, no noticeable changes were found during the study. A slight tendency to an increase in water content during storage at 40° C./75% RH in all doses was seen, though all the test samples were within the preferred range of 4-7%.

Example 11. Determination of Water Content and Water Activity in Allergen Dosage Forms Containing *Phleum pratense* Grass Pollen Extract and Fish Gelatin Composition

TABLE 22

| Name of ingredient | Formulation P (5.5% fish gelatine) | Formulation F (4% fish gelatine) | Function |
|---|---|---|---|
| Purified water | q.s. to 250.00 mg | q.s. to 250.00 mg | Solvent |
| *Phleum pretense* | 2500, 25000, or 75000 SQ-U 0.0047 mg, 0.047 mg, 0.141 mg | 2500, 25000, or 125000 SQ-U 0.0047 mg, 0.047 mg, 0.235 mg | Active substance |
| Gelatine (fishsource) | 16 mg | 10 mg | Matrix |
| Mannitol | 14 mg | 7.5 mg | Matrix |
| Sodium Hydroxide | q.s. to pH 7.5 | q.s to pH 7.5 | pH modifier |

The solid dosage forms were prepared according to example 1.

Water activity of the various solid dosage forms were measured on a Rotronic Hygroskop BT-RS1 (Rotronic ag, Switzerland). 10 tablets were used for each measurement. A stable read out signal indicated that equilibrium was reached, and the relative humidity was subsequently converted to water activity using the following relationship:

$$a_w = \frac{P_w}{P_w^*} = \frac{RH_{equ}}{100}$$

where $a_w$ is the water activity of a sample, $P_w$ is the partial water vapor pressure above a sample, $P_w^*$ is the water vapor pressure above pure water, and $RH_{equ}$ (ERH: relative humidity equilibrium) is the relative humidity of a sample.

A 756 Karl Fischer Coulometer with a 774 Oven Sample Processor (Metrohm, Herisau, Switzerland) was used for the determination of the water content in the tablets. 1-3 tablets were placed in glass vials and sealed with PTFE-coated caps (Metrohm, Herisau, Switzerland). The sample vials were then placed in the 774 Oven Sample Processor (Metrohm, Herisau, Switzerland), and any moisture present in the samples was evaporated at a temperature of 130° C. Evaporated moisture was transferred to the reaction cell containing Hydranal®-Coulomat Oven reagent (Riedel-de-Haen) by nitrogen gas, and a subsequent quantification of the amount of water released was performed by a Karl Fischer titration according to the manufacturer's instructions. The results are presented in table 24.

TABLE 23

Water activity and water content of various allergen dosage forms containing *Phleum pratense* grass pollen extract and fish gelatin.

| | Water activity | | | Water content (%) | | |
|---|---|---|---|---|---|---|
| Sample | N | Mean | SD | N | Mean | SD |
| Placebo, | 3 | 0.46 | 0.022 | 3 | 5.59 | 0.060 |
| P Formulation 2500 SQ-U | 2 | 0.45 | 0.004 | 3 | 4.93 | 0.071 |
| P Formulation 25000 SQ-U | 2 | 0.41 | 0.001 | 3 | 4.67 | 0.021 |
| P Formulation 75000 SQ-U, | 2 | 0.41 | 0.005 | 3 | 4.66 | 0.053 |
| F Formulation 2500 SQ-U | 1 | 0.44 | — | 3 | 5.45 | 0.070 |
| F Formulation 25000 SQ-U | 1 | 0.46 | — | 3 | 5.19 | 0.055 |
| F Formulation 125000 SQ-U | 1 | 0.44 | — | 3 | 4.80 | 0.056 |

SD = standard deviation

All solid dosage forms had a mean water activity between 0.41-0.46, although some had a water content above 5%.

Example 12: Allergen Vaccine Containing *Phleum pratense* Pollen Extract

Composition

TABLE 24

| Ingredients | Composition % w/w | Dosage form 1 Placebo | Dosage form 2 25,000 | Dosage form 3 75,00 |
|---|---|---|---|---|
| Gelatin Fish (Norland, Canada) | 6.0 | 14 mg | 14 mg | 14 mg |
| Mannitol | 5.08 | 12.7 mg | 12.7 mg | 12.7 mg/ |
| API (grass pollen extract) | | 0 | 25,000 SQ-U/ | 75,000 SQ-U |
| NaOH | qs to pH 7.5 | Qs to pH 7.5 | qs to pH 7.5 | qs to pH 7.5 |
| Purified water | qs to 250 mg | qs to 250 mg | qs to 250 mg | qs to 250 mg |
| Total %/Wet fill weight | 100% | 250 mg | 250 mg | 250 mg |
| Dried weight | | 27.7 mg | 27.7 mg | 27.7 mg |

The formulation is manufactured as described in example 1 except that fish gelatin from Norland, Canada is used. The solid dosage form had an average diameter of 13 mm.

TABLE 25

| Dose of dosage form | Friability (% loss of total content of extract (API)) |
|---|---|
| 25.000 SQ-units | 0.000* |
| 75.000 SQ-units | 0.000* |

The results provide a further embodiment of an allergen containing solid dosage form comprising two different doses of grass allergen extract in and matrix forming agent consisting of 6.0% fish gelatin and 5.08% mannitol. The dosage forms were tested in a friability test according to the methods described in example 1. The results show that the formulations are stable in respect of friability as allergen release was detected.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A method for reducing house dust mite-induced allergic symptoms in a patient, said method comprising:
sublingually administering to a patient having at least one clinical allergy symptom of house dust mite-induced allergy a sublingual dosage form containing an effective dose of house dust mite allergen, and repeatedly administering a sublingual dosage form comprising said effective dose of house dust mite allergen daily to said patient, wherein the method does not comprise an up-dosing phase, wherein the repeated administration of said sublingual dosage forms reduces the at least one clinical allergy symptom, and wherein said allergen is a *Dermatophagoides* house dust mite allergen.

2. The method of claim 1, wherein said sublingual dosage form is a tablet.

3. The method of claim 2, wherein said sublingual tablet is packaged in a multiple tablet blister pack comprising multiple tablets.

4. The method of claim 2, wherein the sublingual administration comprises placing the tablet under the tongue for at least 1 minute before swallowing.

5. The method of claim 1, wherein the *Dermatophagoides* house dust mite allergen comprises Der f 1, Der f 2, Der p 1, and Der p 2.

6. The method of claim 1, wherein the at least one clinical allergy symptom is reduced in severity or relieved.

7. The method of claim 1, wherein the at least one clinical allergy symptom is allergic rhinitis.

8. The method of claim 1, wherein the at least one clinical allergy symptom is asthma.

9. The method of claim 1, wherein the *Dermatophagoides* house dust mite allergen is comprised within an extract.

10. The method of claim 9, wherein the *Dermatophagoides* house dust mite extract is a freeze-dried extract.

11. The method of claim 9, wherein the *Dermatophagoides* house dust mite allergen extract comprises the allergens Der f 1, Der f 2, Der p 1, and Der p 2.

12. A method for treating house dust mite-induced allergy in a patient said method comprising:
sublingually administering to a patient having house dust mite-induced allergy a sublingual dosage form containing an effective dose of house dust mite allergen, and repeatedly administering a sublingual dosage form comprising said effective dose of house dust mite allergen daily to said patient, wherein the method does not comprise an up-dosing phase, wherein the repeated administration of said sublingual dosage form treats the house dust mite-induced allergy, and wherein said allergen is a *Dermatophagoides* house dust mite allergen.

13. The method of claim 12, wherein said sublingual dosage form is a tablet.

14. The method of claim 13, wherein said sublingual tablet is packaged in a multiple tablet blister pack comprising multiple tablets.

15. The method of claim 13, wherein the sublingual administration comprises placing the tablet under the tongue for at least 1 minute before swallowing.

16. The method of claim 12, wherein the *Dermatophagoides* house dust mite allergen comprises Der f 1, Der f 2, Der p 1, and Der p 2.

17. The method of claim 12, wherein the house dust mite-induced allergy is reduced in severity or relieved.

18. The method of claim 12, wherein the house dust mite-induced allergy is allergic rhinitis.

19. The method of claim 12, wherein the house dust mite-induced allergy is asthma.

20. The method of claim 12, wherein the *Dermatophagoides* house dust mite allergen is comprised within an extract.

21. The method of claim 20, wherein the *Dermatophagoides* house dust mite extract is a freeze-dried extract.

22. The method of claim 20, wherein the *Dermatophagoides* house dust mite allergen extract comprises the allergens Der f 1, Der f 2, Der p 1, and Der p 2.

23. The method of claim 12, wherein said sublingual dosage form comprises an allergen extract comprising said effective dose of house dust mite allergen.

* * * * *